US012312352B2

(12) United States Patent
Klein et al.

(10) Patent No.: US 12,312,352 B2
(45) Date of Patent: May 27, 2025

(54) USE OF A DPP-4 INHIBITOR IN SIRS AND/OR SEPSIS

(71) Applicant: Boehringer ingelheim International GmbH, Ingelheim am Rhein (DE)

(72) Inventors: Thomas Klein, Radolfzell (DE); Andreas Daiber, Scheessel (DE); Klaus Dugi, Dresden (DE); Michael Mark, Biberach an der Riss (DE); Thomas Muenzel, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/730,470

(22) Filed: Apr. 27, 2022

(65) Prior Publication Data

US 2022/0340575 A1    Oct. 27, 2022

Related U.S. Application Data

(63) Continuation of application No. 16/296,353, filed on Mar. 8, 2019, now abandoned, which is a continuation of application No. 13/892,377, filed on May 13, 2013, now abandoned.

(30) Foreign Application Priority Data

May 14, 2012    (EP) .................... 12167893

(51) Int. Cl.
| | | |
|---|---|---|
| *A61K 31/522* | (2006.01) | |
| *A61K 31/4985* | (2006.01) | |
| *A61K 31/5025* | (2006.01) | |
| *A61K 31/519* | (2006.01) | |
| *A61K 45/06* | (2006.01) | |
| *C07D 473/06* | (2006.01) | |

(52) U.S. Cl.
CPC ........ *C07D 473/06* (2013.01); *A61K 31/4985* (2013.01); *A61K 31/5025* (2013.01); *A61K 31/519* (2013.01); *A61K 31/522* (2013.01); *A61K 45/06* (2013.01)

(58) Field of Classification Search
CPC ................................................ A61K 31/4985
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Salvin |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,159,345 A | 6/1979 | Takeo et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,764,466 A | 8/1988 | Suyama et al. |
| 4,816,455 A | 3/1989 | Schickaneder et al. |
| 4,873,330 A | 10/1989 | Lindholm |
| 4,968,672 A | 11/1990 | Jacobson et al. |
| 5,034,225 A | 7/1991 | Bennett et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Toshiaki, ABC18 for new diagnostics and treatments, The medical frontline, 2004, p. 106-112.

(Continued)

*Primary Examiner* — Yong S. Chong
(74) *Attorney, Agent, or Firm* — David L. Kershner

(57) ABSTRACT

The present invention relates to methods for treating and/or preventing SIRS and/or sepsis comprising the administration of an effective amount of a certain DPP-4 inhibitor, as well as to the use of a certain DPP-4 inhibitor for treating and/or preventing a metabolic disease in a patient with or at risk of SIRS and/or sepsis.

8 Claims, 2 Drawing Sheets

Specification includes a Sequence Listing.

(56) References Cited

U.S. PATENT DOCUMENTS

| | | |
|---|---|---|
| 5,777,115 A | 7/1998 | Leigh et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,399,101 B1 | 6/2002 | Frontanes et al. |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Asahi |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 7,919,572 B2 | 4/2011 | Angot et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 9,486,526 B2 | 11/2016 | Dugi |
| 9,493,462 B2 | 11/2016 | Sieger |
| 9,815,837 B2 | 11/2017 | Sieger |
| 10,023,574 B2 | 7/2018 | Himmelsbach |
| 10,034,877 B2 | 7/2018 | Dugi |
| 10,092,571 B2 | 10/2018 | Dugi et al. |
| 10,155,000 B2 | 12/2018 | Meinicke et al. |
| 10,301,313 B2 | 5/2019 | Sieger et al. |
| 10,973,827 B2 | 4/2021 | Friedl et al. |
| 11,033,552 B2 | 6/2021 | Kohlrausch et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0042393 A1 | 4/2002 | Oobae et al. |
| 2002/0049164 A1 | 4/2002 | Demuth et al. |
| 2002/0115718 A1 | 8/2002 | Chen et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0018468 A1 | 1/2004 | Gorokhovsky |
| 2004/0023981 A1 | 2/2004 | Ren et al. |
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097410 A1 | 5/2004 | Zheng et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |

(56) References Cited

U.S. PATENT DOCUMENTS

| | | |
|---|---|---|
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259843 A1 | 12/2004 | Madar et al. |
| 2004/0259903 A1 | 12/2004 | Boehringer et al. |
| 2004/0266806 A1 | 12/2004 | Sanghvi et al. |
| 2005/0020484 A1 | 1/2005 | Harada |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0031682 A1 | 2/2005 | Cucala Escoi et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0070694 A1 | 3/2005 | Gelfanova et al. |
| 2005/0097798 A1 | 5/2005 | Evans et al. |
| 2005/0107730 A1 | 5/2005 | Doty et al. |
| 2005/0119162 A1 | 6/2005 | Harada et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0008829 A1 | 1/2006 | Hess |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Yer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259880 A1 | 11/2007 | Sakashita et al. |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0221200 A1 | 9/2008 | Allison et al. |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0054303 A1 | 2/2009 | Gougoutas et al. |
| 2009/0082256 A1 | 3/2009 | Abe et al. |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0253752 A1 | 10/2009 | Burkey et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0206766 A1 | 8/2011 | Friedl et al. |
| 2011/0212982 A1 | 9/2011 | Christopher et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |

(56) References Cited

U.S. PATENT DOCUMENTS

| | | |
|---|---|---|
| 2013/0236543 A1 | 9/2013 | Ito et al. |
| 2013/0303462 A1 | 11/2013 | Klein |
| 2013/0303554 A1 | 11/2013 | Klein et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0010509 A1* | 1/2015 | Moheno ............ A61K 31/7072 514/230.2 |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0089373 A1 | 3/2016 | Johansen et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |
| 2017/0354660 A1 | 12/2017 | Meinicke et al. |
| 2021/0299120 A1 | 9/2021 | Gupta |
| 2022/0378797 A1 | 12/2022 | Friedl et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CN | 101035522 A | 9/2007 |
| CN | 101234105 A | 8/2008 |
| CN | 101309689 A | 11/2008 |
| CN | 101590007 A | 12/2009 |
| CN | 104130258 A | 11/2014 |
| CN | 104418857 A | 3/2015 |
| CN | 105272982 A | 1/2016 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0289282 A2 | 11/1988 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1604989 A1 | 12/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| EP | 2308878 A2 | 4/2011 |
| EP | 3646859 A1 | 5/2020 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 61030567 | 2/1986 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004196824 A | 7/2004 |
| JP | 2004250336 A | 9/2004 |
| JP | 2006503013 A | 1/2006 |
| JP | 2006045156 A | 2/2006 |
| JP | 2006137678 A | 6/2006 |
| JP | 2007501231 A | 1/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |
| JP | 2010070576 A | 4/2010 |
| JP | 2010524580 A | 7/2010 |
| JP | 2010536734 A | 12/2010 |
| JP | 2011088838 A | 5/2011 |
| JP | 2011529945 A | 12/2011 |
| JP | 2012505859 A | 3/2012 |
| KR | 20070111099 A | 11/2007 |
| WO | 8706941 A1 | 11/1987 |
| WO | 199107945 A1 | 6/1991 |
| WO | 199205175 A1 | 4/1992 |

(56) References Cited

FOREIGN PATENT DOCUMENTS

| | | |
|---|---|---|
| WO | 199219227 A2 | 11/1992 |
| WO | 199308259 A2 | 4/1993 |
| WO | 199402150 A1 | 2/1994 |
| WO | 199403456 A1 | 2/1994 |
| WO | 1994012200 | 6/1994 |
| WO | 9532178 A1 | 11/1995 |
| WO | 199609045 A1 | 3/1996 |
| WO | 199611917 A1 | 4/1996 |
| WO | 199636638 A1 | 11/1996 |
| WO | 199718814 A1 | 5/1997 |
| WO | 199723447 A1 | 7/1997 |
| WO | 199723473 A1 | 7/1997 |
| WO | 199728808 A1 | 8/1997 |
| WO | 199746526 A1 | 12/1997 |
| WO | 1998007725 | 2/1998 |
| WO | 199811893 | 3/1998 |
| WO | 9818770 A1 | 5/1998 |
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 9903854 A1 | 1/1999 |
| WO | 199929695 A1 | 6/1999 |
| WO | 1999038501 A2 | 8/1999 |
| WO | 199950248 A1 | 10/1999 |
| WO | 1999049857 | 10/1999 |
| WO | 199956561 A1 | 11/1999 |
| WO | 199967279 A1 | 12/1999 |
| WO | 2000003735 A1 | 1/2000 |
| WO | 200012064 A1 | 3/2000 |
| WO | 200072873 | 5/2000 |
| WO | 200034241 A1 | 6/2000 |
| WO | 0069464 A1 | 11/2000 |
| WO | 200066101 A2 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003006425 A2 | 1/2003 |
| WO | 2003024965 A2 | 3/2003 |
| WO | 2003033686 A2 | 4/2003 |
| WO | 03038123 A2 | 5/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003057245 A1 | 7/2003 |
| WO | 2003059327 | 7/2003 |
| WO | 2003061688 A1 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A1 | 10/2005 |
| WO | 2005107730 A2 | 11/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2005119526 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |

(56) References Cited

FOREIGN PATENT DOCUMENTS

| | | |
|---|---|---|
| WO | 2006129785 A1 | 12/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 07035665 A1 | 3/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008017670 A1 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 | 2/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 199967278 | 12/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010126908 A1 | 11/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2012031124 A2 | 3/2012 |
| WO | 2012039420 A1 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014029848 A1 | 2/2014 |
| WO | 2014140284 A1 | 9/2014 |
| WO | 2014170383 A1 | 10/2014 |
| WO | 2017047970 A1 | 3/2017 |
| WO | 2020016232 | 1/2020 |
| WO | 2020016232 A1 | 1/2020 |

OTHER PUBLICATIONS

The Japan Diabetes Society, Guidelines for treatment of Diabetes, Feb. 14, 2006, p. 21-33, 41-55, 62-76.
Yamaguchi, Today's Therapeutic Guidelines, 2006, p. 518-520.
Sakura, Trends in development on oral diabetic agents and new developments of treatment, Clinical Endocrinology, vol. 3, 2011, p. 51-55.
Yoshimoto, Structure of DPP-4 and Antidiabetic Therapeutic Agents, Current Diabetology, vol. 3, p. 51-55.
Kawamori, Investigation of Diabetes, Soten Lmtd., 2004, p. 15-19.
Shigeta, MR Training Manual, Elsevier, 2004, p. 44-54, p. 67-74.
Ono, Diabetes and islet tranplantation, Japanese J. of clinical Pathology, vol. 54, 2006, p. 379-385.
Suzuki, Prospects of ISlet transplantation, Pharma medica, vol. 24, 2006, p. 67-71.
Shimada, MR Training Manual, Cardiovascular System, Elsevier, 2003, p. 2-58.
Kazunaga, Guidelines for Required dose Response, Pharmaceutical Examination, 1994, 1 page.
Ministry of Health, Clinical Pharmacokinetics Examination of Druge, vol. 796, 2001, 1 page.
Uematsu, Text of clinical Pharmacology, Nancodo, 1997, p. 45-51.
National Library of Medicine, Searching result of information for Clinical Trial NCT00309608 for Linagliptin from Clinicaltrials.gov, Mar. 31, 2006.
Boehringer Ingelheim Japan, Interview Form for Trazenta Tablets 5 mg, Apr. 2022, 18 version.
Katakami, Action and usage of oral hypoglycemic agents, Clinica, vol. 31, 2004, p. 398-399.
Sanwa Kagaku Kenkyusho, Package Insert fo Seibule tablets 25mg, 50 mg, 75mg, Aug. 2021.
Funabashi, Basic concept for metabolic syndrome, Pharma medica, vol. 22, 2004, p. 11-16, 21-24.
Kita, Satin based anti-arteriosclerotic drugs, vol. 32, 2000, p. 932-936.
Viatris Pharmaceuticals, Package Insert for Lipitor, 10mg. Nov. 2022.

(56) References Cited

OTHER PUBLICATIONS

Sun Pharma Japan Limited, Package insert for Lopresor Tablet, 20mg, 40mg, Oct. 2021.
Sumitomo Pharma Co., Package insert for AmlodinTablets, 2.5mg, 5mg, 10mg, and Amlodin MD Tablets, 2.5mg, 5mg, 10mg, Dec. 2022.
Pfizer Lab Division, Inc., Drug Label for Altace Ramipril Casules, Feb. 2022.
Novartis Pharma, K.K. Package Insert for Diovan Tablets, 20mg, 40mg, 80mg, 16omg, Apr. 2020.
Boehringer Ingelheim Japan, Package insert for Micardis Tablets, 20mg, 40mg, 80mg, Jul. 2020.
Viatros Pharmaceuticals, Co., Ltd., Interview form for Lipitor Tablets, 5mg, 10mg, Dec. 2022.
Hotchkiss, The pathophysiology and Treatment of Sepsis, The New England J. of Medicine, vol. 348, 2003, 13 pages.
Russell, Treatment of Sepsis, New England J. of Medicine, vol. 355, 2006, 15 pages.
Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.
International Search Report and Written Opinion for PCT/EP2011/057256 mailed Jul. 22, 2011.
Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic fatty-liver-disease/DS00577DSECTION=prevention>.
Shanks, N. et al., Are animal models predictive for humans?, PEHM, Philosophy, Ethics, and Humanaities in Medicine, 4(2), 2009, 1-20.
Hermann, Robert, et al; Lack of Association of PAX4 Gene with Type 1 Diabetes in the Hungarian Populations; Diabetes (2005) vol. 54 pp. 2816-2819.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hayashi, Michio., "Recipe for Oral Hypoglycemic Agents to Pathological Condition" Pharmacy (2006) vol. 57, No. 9 pp. 2735-2739.
Komori, Kiyoshi., "Treatment of Diabetes in Patients for Whom Metforming Treatment is Not Appropriate" Modern Physician (2008) vol. 28, No. 2 pp. 163-165.
Matsumiya, Teruhiko, et al., "Therapeutic Drugs for Clinicians" Diagnosis and Treatment (2008) vol. 96, No. 2 pp. 389-390.
Shintani, Maki, et al., "Insulin Resistance and Genes" Circulatory Sciences (1997) vol. 17, No. 12 pp. 1186-1188.
Kharkevich, D. A., "Educational Literature" Pharmacology (1987) Third Edition, Meditsina Press, Moscow pp. 47-48.

Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Clinical Trial NCT00622284 (published online at clinicaltrials.gov on Feb. 22, 2008).
Anstee, Quentin M. et al. "Mouse models in non-alcholic fatty liver disease and steatohepatitis research" (2006) International Journal of Expermental Pathology, vol. 87, pp. 1-16.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." DIabetes Obesity and Metabolism, 2007, vol. 9, No. 2, pp. 194-205.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Tounyoubyou, "Symposium-19: Future Perspectives on Incretion Therapy in Diabetes." 2008, vol. 51, Suppl. 1, p. S-71, S19-2.
Plummer, C.J.G et al., "The Effect of Melting Point Distributions on DSC Melting Peaks." Polymer Bulletin, 1996, vol. 36, pp. 355-360.
Office Action for U.S. Appl. No. 10/695,597 mailed May 2, 2008.
Tribulova, N. et al. "Chronic Disturbances in NO Production Results in Histochemical and Subcellular Alterations of the Rat Heart." Physiol. Res., 2000, vol. 49, No. 1, pp. 77-88.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Tradjenta, Highlights of Prescribing Information (revised Sep. 2012).
Inukai, T., "Treatment of Diabetes in Patients for Whom Metformin Treatment is Not Appropriate." Modern Physician, 2008, vol. 28, No. 2, pp. 163-165.
Gennaro, Alfonso R., Remington Farmacia, 19th Edition, Spanish copy, 1995, p. 2470.
Berge, S. et al., "Pharmaceutical Salts." Journal of Pharmaceutical Sciences, 1977, vol. 66, No. 1, pp. 1-19.
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Diabetes Frontier, 2007, vol. 18, No. 2, p. 145-148.
Geka, 2001, vol. 67, No. 11, p. 1295-1299.
Nihon Ijinpo, Japan Medicinal Journal, 2001, No. 4032, p. 137.
Definition of "prevent", e-dictionary, Aug. 15, 2013, http://dictionary.reference.com/browse/prevent.
Medline Plus, "Obesity" 2013, Retrieved from internet on Aug. 22, 2013, http://www.nlm.nih.gov/medlineplus/obesity.html.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Ferry, Robert Jr., "Diabetes Causes." eMedicine Health, MedicineNet.com, 2013, Retrieved from internet on Aug. 22, 2013, <http://www.onhealth.com/diabetes_health/page3.htm#diabetes_causes>.
United Healthcare, "Diabetes." Retrieved from internet on Aug. 22, 2013, http://www.uhc.com/source4women/ health_topics/

(56) References Cited

OTHER PUBLICATIONS diabetesirelatedinformation/
dOf0417b073bf11OVgnVCM1000002f1Ob1Oa_.htm.
Florez, J. et al. "TCF7L2 Polymorphisms and Progression to Diabetes in the Diabetes Prevention Program." The New England Journal of Medicine, 2006, vol. 355, No. 3, pp. 241-250.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Diabetesincontrol.com "EASD: Eucreas, a Combination of Galvus and Metformin, Recommended for Approval." Diabetes In Control. com, Sep. 25, 2007, Retrieved from internet on Nov. 30, 2012, http://www.diabetesincontrol.com/articles/53-diabetes-news/5145.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Drucker, et al.., The incretin system:glucagon-like peptide-1 receptor agonists and dipeptidyl peptidase-4 inhibitors in type 2 diabetes. Lancet, 2006, 368: 1696-705.
Horsford, E. N. "On the source of free hydrochloric acid in the gastric juice." Proceedings of the Royal Society of London, Published in 1868-1869, vol. 17, pp. 391-395.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.
Baetta, R. et al., "Pharmacology of Dipeptidyl Peptidase-4 Inhibitors." Drugs, 2011, vol. 71, No. 11, pp. 1441-1467.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Naik, R. et al., "Latent Autoimmune Diabetes in Adults." The Journal of Clinical Endocrinology and Metabolism, 2009, vol. 94, No. 12, pp. 4635-4644.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Somaa, B. et al., "Cardiovascular Morbidity and Mortality Associated With the Metabolic Syndrome." Diabetes Care, 2001, vol. 24, No. 4, pp. 683-689.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Crowe, E. et al., "Early identification and management of chronic kidney disease: summary of NICE guidance." British Medical Journal, 2008, vol. 337, pp. 812-815.
Hull, R. et al., "Nephrotic syndrome in adults." British Medical Journal, 2008, vol. 336, pp. 1185-1190.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Cheon, et al., Biochemical Pharmacology, "Inhibition of dipeptidyl IV by novel inhibitors with pyrazolidine scaffold", 2005, vol. 70, p. 22-29.
Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.
International Search Report and Written Opinion for PCT/EP2015/054114 mailed May 12, 2015.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Zhimei, Xiao et al., "Study progression of oral drugs for treatment of type II diabetes." Drug Evaluation, 2004, vol. 1, No. 2, pp. 138-143.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
Vichayanrat, A. et al., "Efficacy and safety of voglibose in comparison with acarbose in type 2 diabetic patients." Diabetes Research and Clinical Practice, 2002, vol. 55, pp. 99-103.
Takeda Press Release: "Voglibose (Basen) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.
Weber, Ann E., "Dipeptidyl Peptidase IV Inhibitors for the Treatment of Diabetes." Journal of Medicinal Chemistry, 2004, vol. 47, pp. 4135-4141.
WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.
Oz, Helieh S., "Methionine Deficiency and Hepatic Injury in a Dietary Steatohepatitis Model." Digestive Diseases and Sciences, 2008, vol. 53, No. 3, pp. 767-776.
Ahren, Bo "Novel combination treatment of type 2 diabetes DPP-4 inhibition + metformin." Vascular Health and Risk Management, 2008, vol. 4, No. 2, pp. 383-394.
Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Clinical Trials, No. NCT00309608, "Efficacy and Safety of BI 1356 BS in Combination with Metformin in Patients With type2 Diabetes" 2009, pp. 1-3.
Hammouda, Y. et al., "Lactose-induced Discoloration of Amino Drugs in Solid Dosage Form." Die Pharmazie, 1971, vol. 26, p. 181.
Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Kumar, V. et al., "Maillard Reaction and Drug Stability." Maillard Reactions in Chemistry, Food, and Health, 1994, No. 151, pp. 20-27.
Castello, R. et al., "Discoloration of Tablets Containing Amines and Lactose." Journal of Pharmaceutical Sciences, 1962, vol. 51, No. 2, pp. 106-108.
Yoshioka, S. et al., "Stability of Drugs and Dosage Forms." Kluwer Academic Publishers, 2002, pp. 30-33.
Nabors, Lyn O'Brien "Alternative Sweeteners." Marcel Dekker, Inc., 2001, pp. 235, 339-340.
Lieberman, H. et al., "Pharmaceutical Dosage Forms." Marcel Dekker, Inc., 1980, vol. 1, p. 38.
Rowe, R. et al., Handbook of Pharmaceutical Excipients, Fourth Edition, Pharmaceutical Press and American Pharmaceutical Association, 2003, pp. 323-332., 373-377, 609-611.
Eyjolfsson, Reynir "Lisinopril-Lactose Incompatibility." Drug Development and Industrial Pharmacy, 1998, vol. 24, No. 8, pp. 797-798.
Canadian Pharmacists Association, Compendium of Pharmaceuticals and Specialties, "Zestril" 2004, pp. 2289-2293.

(56) References Cited

OTHER PUBLICATIONS

Scientific Discussion, EMEA, Pramipexole, 2005, pp. 1-10.
Gennaro, Alfonso; Remington: The Science and Practice of Pharmacy, Twentieth Edition, 2000, Chapter 45, pp. 860-869.
Aulton, Michael E., Pharmaceutics: The Science of Dosage Form Design, Second Edition, 2002, pp. 441-448.
MIMS Jan. 2009, "Sitagliptin." pp. 152-153.
EMEA: European Medicines Agency, ICH Topic E4, "Dose Response Information to Support Drug Registration." 1994, pp. 1-10.
"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70120>.
"Sifrol 0,18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0:SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70124>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.
"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,57626>.
Kroller-Schuhmacher, Comparison of direct and indirect antioxidant effects of linagliptin with other gliptins, Vascular Pharmacology, vol. 56, 2012, p. 352.
Schuff, Comparison of the Direct and indirect Antioxidant Effects of DPP-4 Inhibitors, retrieved from https://professional.diabetes.org/abstract/comparison-direct-and-indirect-antioxidant-effects-dpp-4-inhitors-anti-inflammatory 2011, 1 page.
Singh, Sepsis in diabetes, Diabetes and metabolic Syndrome, Clinical Research and Reviews, vol. 5, 2011, p. 222-227.
Fink, Animal models of sepsis and its complications, Kidney International, vol. 74, 2008, p. 991-993.
Galley, Oxidative stress and mitochondrial dysfunction in sepsis, British J. of Anaesthesia, vol. 107, 2011, p. 57-64.
Baudouin, Sepsis, Springer-Verlag, vol. 88, 2008, p. 1-4.
Freeman, Efficacy and Safety of Linagliptin in Adults with type 2 diabetes, vol. 36, 2011, p. 807-842.
UK Prospective Diabetes Study Group, Intensive blood glucose control with sulphonylureas or insulin compared withconventional treatment and risk of complications in patients with type 2 diabetes, The Lancet, vol. 352, 1998, p. 837-853.
Scherbaum, Sepsis, Psychyrembel Worterbach Diabetologie, 2003.
Schuermann, The Didpeptidyl Peptidase-4 inhibitor linagliptin attentuates inflammation and accelerates epitheliaixation in wounds of diabetic ob/ob mice, J. of pharmacology and experimental therapeutics, 2012, 8 pages.
Arenson, Neuropathy, Aniopathy, and sepsis in the diabetic foot, J. of american Podiatry assoc., vol. 72, 1982, p. 35-40.
Andrades, Bench to bedside review, Sepsis, from the redox point of view, Clinical care, vol. 15, 2011, 8 pages.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones heterocycliques. IV. Synthèses de dérivés de l'hydrazine dans la serie des imidazo[4,5-d]pyridazinones-4, Can. J. Chem., vol. 61, No. 11, 1983, pp. 2563-2566.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Brittain, H.G., "Methods for the Characterization of Polymorphs: X-Ray Powder Diffraction," Polymorphism in Pharmaceutical Solids, 1999, p. 235-238.
Busso et al., "Circulating CD26 is Negatively Associated with Inflammation in Human and Experimental Arthritis," Am. J. Path., vol. 166, No. 2, Feb. 2005, pp. 433-442.
Caira, M.R., "Crystalline polymorphism of organic compounds" Topics in Current Chemistry, Springer, Berlin, vol. 198, 1998, p. 163-208.
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Cygankiewicz, Andrzej et al., Investigations into the Piperazine Derivatives of Dimethylxanthine:, ACTA Polon. Pharm. [Papers of Polish Pharmacology], XXXOV, No. 5, pp. 607-612, 1977.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
DeMeester, I. et al.; "CD26, let it cut or cut it down", Review: Immunology Today; Aug. 1999, vol. 20, No. 8 pp. 367-375.
Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.
Patani George A. et al.: "Bioisoterism : A Rational Approach in Drug Design", Chemical Reviews, 1996, vol. 96, No. 8, pp. 3147-3176.
Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Tanaka, S.. et al; "Suppression of Arthritis by the Inhibitors of Dipeptidyl Peptidase IV," In. J. Immunopharmac., vol. 19, No. 1, pp. 15-24, 1997.
Wolff, M.E.: "Burger's Medicinal Chemistry and Drug Discovery" Fifth Edition, vol. 1: Principles and Practice, pp. 975-977, 1994, John Wiley & Sons, Inc.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Zhong, Qing et al; "Glucose-dependent insulinotropic peptide stimulates proliferation and TGF-? release from MG-63 cells," Peptides 24 (2003) 611-616.
International Search Report and Written Opinion for PCT/EP2007/054270 mailed Aug. 14, 2007.
International Search Report and Written Opinon for PCT/EP2007/054204 mailed Aug. 3, 2007.
International Search Report and Written Opinion for PCT/EP2007/054201 mailed Aug. 29, 2007.
Priimenko, B. A., et al; Synthesis and Pharmacological Activity of Derivates of 6,8-Dimethyl Imidazo(1,2-f)Xanthine-(Russ.); Khimiko-Farmatsevticheskii zhurnal (1984) vol. 18, No. 12 pp. 1456-1461.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Zejc, Alfred, et al; "Badania Nad Piperazynowymi Pochodnymi Dwumetyloksantyn" Acta Polon Pharm, XXXV (1976) Nr. 4 pp. 417-421.

(56) References Cited

OTHER PUBLICATIONS

International Search Report for PCT/EP2005/055711 dated Mar. 29, 2006.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Giron, D.; Thermal Analysis and Calorimetric Methods in the Characterisation of Polymorphs and Solvates; Thermochimica Acta (1995) vol. 248 pp. 1-59.
Thomas, Leo et al: "(R)-8-(3-Amino-piperidin-1-yl)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor . . . " Journal of Pharmacology and Experimental Therapeutics, 2008, vol. 325, No. 1, pp. 177.
International Search Report and Written Opinion for PCT/EP2008/060740 mailed Mar. 30, 2009.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 Inhibitor for the treatment of type 2 diabetes: Journal of Medicinal Chemistry, American Chemical Society. Washington.; US, vol. 50, No. 26, Dec. 1, 2007, p. 6450-6453.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
Huettner Silks et al: "BI 1356, a novel and selective xanthine based DPP-IV inhibitor, demonstrates good safety and tolerability with a wide therapeutic window" Diabetes< American Diabetes Association, US, vol. 56, no. Suppl 1, Jun. 1, 2007, p. A156.
International Search Report and Written Opinion for PCT/EP2010/050103 mailed Mar. 22, 2010.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Medicine Department of Pharmacy, Pharmaceutical Subcommitte, Book Publishing Harwinton, 1996, p. 283.
Huang, et al. Elimination of metformin-croscarmellose sodium interaction by competition, International Journal of Pharmaceutics, 2006, p. 33-39.
"Freeman, Initial Combination therapy for patients with type 2 diabetes mellitus", Drugs in Context, 2013, p. 212256., 6 pages.
Scheen, Efficacy and Safety of Jentadueto, Expert Opinion on Drug and Safety, vol. 12, No., 2, 2013, p. 275-289.
Haak, Initial Combination of linagliptin and metformin improves glycemic control in type 2 diabetes, Diabetes, Obesity and Metabolism, vol. 14, 2012, p. 565-574.
International Search Report and Written Opinion for PCT/EP2017/064007, mailed Jun. 8, 2017.
Wikipedia, the free encyclopedia, The carbonyl group, 2017, 1 page.
Controlling Temperature (Guidelines for the Storage of Essential Medicines and Other Health Commodities, 2003, http://apps.who.int.medicinedocs/en/d/Js4885e/6.5html), 5 pages.
Pharmaceutical Manufacturing and Storage (Concepts and Design, Inc.) 2009.
Methocel Cellulose Ethers in Aqueous Systems for tablet coating: retrieved from Internet: http;//msdssearch.dow.com/PublishedLiterature DOWCOM/dh_004a/0901b8038004ab56.pdf?filepath=198-00755.pd?fromPage=GetDoc, published2002. Retrieved Dec. 8, 2017, 3 pages.
Wu, Reactive Impurities in Excipients-Profiling, American Association of Pharmaceutical Scientists, 2011, vol. 12, No. 4, p. 1248-1263.
Waterman, Accelerating aging-Prediction of Chemical Stability of Pharmaceuticals, International Journal of Pharmaceutics, 2005, vol. 293, p. 101-125.
Kaur, Development of new incretin drugs: Promising Therapies, Indian Journal Pharmacology, 2006, vol. 38, Issue 2, p. 100-106.
Clinical Trial results of Tradjenta Tablet, Center for Drug Evaluation and Research, 2010.
Pregelatinized Starch, Drugs.com, derived from https://drugs.com/inactive/pregelatinized-starch-136.html, accessed Nov. 17, 2017.
Approval material for Tradjenta tablet, Trial 1218.2, Center for Drug Eval. and Research, 2011.
Hu, Diabetes Mellitus and Cardiovascular Disease, People's Military Medical Press, 2005, p. 211.
Susman, Ada: Linagliptin Works in Diabetic Kidney Disease, Med Page Today, 2011, 2 pages.
Okano, Renal Clearance, New General Pharmaceutics, Revised 3rd Edition, 1987p. 213-215.
Clinical trials, A Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Eckhardt, "-(3-(R)-Aminopiperidin-1-yl)7-but-2-ynyl-3-methyl-1-(4-methyl-quinazolin-2-ylmethyl-3,7-dihydropurine-2,6- dione (BI 1356), a highly potent, selective, long-acting, and orally bioavailable DPP-4 inhibitor for the treatment of type 2 diabetes", J. med. Chem, vol. 50, 2007.
Shigai, "How to use medicines in case of kidney injury caused by medicine" Journal of the Japanese Association of Rural Medicine, vol. 51, 2002, p. 63-67.
Zeng, "Efficacy and Safety of linagliptin added to metformin and sulphonylurea in Chinese patients with type 2 diabetes: a sub-analysis of data from a randomised clinicial trial", Current Medical Research and Opinion, 2013, 8 pages.
Seino, Alogliptin plus voglibose in Japanese patients with type 2 diabetes: a randomized, double blind, placebo-controlled trial with an open label, long term extension, Current Medical Research and Opinion, 2011, vol. 27, p. 21-29.
Kurozumi, Efficacy of a-glucosidase inhibitors combined with dipeptyl-peptidase-4 inhibitor for glucose fluctuation in patients with type 2 diabetes mellitus by continuous glucose monitoring, Journal of Diabetes Investigation, 2013, vol. 4, p. 393-398.
Horikawa, Synergistic Efffect of a-glucosidase inhibitors and dipeptidyl peptidase 4 inhibitor treatment, Journal of Diabetes Investigation, 2011, vol. 2, p. 200-203.
Yamazaki, Comparison of Efficacies of a Dipeptidyl Peptidase IV Inhibitor and a-Glucosodase Inhibitors in Oral Carbohydrate and Meal Tolerance Tests and their Effects of their tolerance in mice, J. Pharmacol Science, 2007, p. 29-38.
Kawamori, Linagliptin monotherapy provides superior glycaemic control v. placebo or voglibose with comparable safety in Japanese patients with type 2 diabetes, a randomized , placebo and active comparator-controlled doiuble blind study, 2011, Diabetes, Obesity and Metabolism, p. 348-357.
Inagaki, Linagliptin provides effective, well-tolerated add-on therapy to pre-existing oral antidiabetic therapy over 1 year in Japanese patients with type 2 diabetes, Diabetes, Obesity and Metabolis, 2013, p. 833-843.
Tang, Protection of DPP-4 inhibitors on cardiovascular, Drug Evaluation, vol. 9, 2012, p. 6-9.
Han, Basic and Clinical Coronary Heart Disease, Jilin Univ. Press, 2012, p. 114-118.
Lakey, Technical Aspects of Islet Preparation, Translp, Int.m 2003, vol. 16, p. 613-632.

(56) References Cited

OTHER PUBLICATIONS

White, Cardiovascular Events in patients receiving alogliptin, Diabetes Pro, 2010, vol. 59, p. 391.
Johansen, Cardiovascular safety with linagliptin on patients with type 2 diabetes mellitus, Cardiovascular Diabetology, 2012, vol. 11, p. 1-10.
Pham, New Onset Diabetes Mellitus After Solid Organ Transplantation, Endocrinology and Metabolism Clinics of North America, 2007, p. 873-890.
Nursten, The Mailard Reaction, Chemistry, Biochemistry, and Implications, Chapter 10, 2018, p. 1-8.
DiFeo, Drug Product Development, A Technical Review of Chemistry, Drug Development and Industrial Pharmacy, vol. 29, 2003, p. 939-958.
Federal register, Department of Health and Human Services, vol. 62, 1997, 4 pages.
Nachaegari, Coprocessed Excipients for Solid Dosage Forms, Pharmaceutical technology, 2004, 8 pages.
Ahmed, Materials Formulation of Low Dose Medicines, Americal Pharma review, vol. 3, 2000, 1 page.
Wikipedia, Polyvinylpyrrolidone, https:en.wikipedia.org/wiki/ access date May 15, 2018.
Westerhuis, Optimisation of the composition and production of mannitol cellulose tablets International Journal of Pharmaceutics, 1996, p. 143, 151-162.
Portincasa, Current Pharmacological Treatment of Nonalcoholic Fatty Liver, Current Medicinal Chem, 2006, p. 2889-2900.
Del Prato, Diabetes, Obesity and Metabolism, Effect of linagliptin monotherapy on glycemic control and markers of b-cell function in patients with inadequately controlled type 2 diabetes: a randomized controlled trial, 2011, p. 258-267.
Gallwitz, linagliptin-A novel Dipeptidyl Peptidase Inhibitor for Type 2 Diabetes Therapy, Clinical Medicine Indights: Endocrinology and Diabetes, 2012, vol. 5, p. 1-11.
Mikhail, Investigating Drugs, Incretin Mimetics and dipeptidyl peptidase 4 inhibitors in clinical trials for the treatment of Type 2 diabetes, vol. 17, 2008, p. 845-853.
Cefalu, Animal Models of Type 2 Diabetes: Clinical Presentation and Pathophysiological Relevance to the Human Condition, ILAR Journal, vol. 47, No. 3, 2006.
Zaman, Comparison Between Effect of Vildagliptin and Linagliptin on Glycaemic control, renal function, liver funstion and lipid profile in patients of T2DM Inadequately controlled with combo of Metformin and Glimepiride, Journal of Dental and Medical Sciences, vol. 16, Issue 9, 2017. p. 27-31.
Connelly, Dipeptyl peptidase-4 inhibition improves left ventricular function in chronic kidney disease, Clinical and Investigative Medicine, vol. 37, 2014, p. 172-185.
Scheen, Clinical Pharmacokinetics of metformin, Clinical Pharmacokinetics, vol. 30, No. 5, 1996, p. 359-371.
International Search Report and Written Opinion for PCT/EP2009/067772 mailed Apr. 14, 2010.
Greene, T.W, et al., "Protection for the Amino Group". Protective Groups in Organic Synthesis, 3rd edition, 1999, p. 494-653.
Dave, K.G. et al., "Reaction of Nitriles under Acidic Conditions, Part I. A General Method of Synthesis of Condensed Pyrimidines", J. Heterocyclic Chemistry, BD, 17, 1, Issn 0022-152X, Nov. 1980, p. 1497-1500.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
International Search Report and Written Opinion for PCT/EP2010068349 mailed Feb. 4, 2011.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00798161. "Safety and efficacy of Bi 1356 Plus Metformin in Type 2 Diabetes, Factorial Design". Clinical Trials. gov archive. A Service of the U.S> National Institutes of Health. Nov. 24, 2008, p. 1-3. http://clinicaltrials.gov/archive/NCT00798161/2008_11_24.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?ald=96695.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Thomas, L. et al, "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.
Ahren, Bo; "DPP-4 inhibitors", Best practice and research in clinical endocrinology and metabolism—New therapies for diabetes 200712 GB LNKD- DOI:10.1016/J. Beem.2007.07.005, vol. 21, No. 4, Dec. 2007, pp. 517-533.
International Search Report for PCT/EP2010/064691 mailed Jan. 20, 2011.
International Search Report and Written Opinion for PCT/EP2009/063511 mailed Feb. 26, 2010.
International Search Report and Written Opinion for PCT/EP2010/051093 mailed Jul. 14, 2010.
Bundgaard, H. "Design of prodrugs: Bioreversible derivatives for various functional groups and chemical entities". Royal Danish School of Pharmacy, 1985, p. 1-92.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
X-Ray Diffraction. The United States Pharmacopeia, 2002, USP 25 NF20, p. 2088-2089.
Chemical Abstract: No. 211513-37-0—Dalcetrapib. "Propanethioic acid, 2-methyl-,S-(2-[[1-(2-ethylbutyl)cyclohexyl}carbonyl}amino}pheyl}ester" . Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Augusti, D.V. et al., "Quantitative determination of the enantiomeric composition of thalidomide solutions by electrospray ionizatio tandem mass spectrometry". Chem Comm, 2002, p. 2242-2243.
International Search Report and Written Opinion for PCT/EP2011/057163 mailed Jun. 27, 2011.
International Search Report and Written Opinion for PCT/EP2011/054169 mailed Aug. 4, 2011.
Jones, R.M. et al., "GPR119 agonists for the treatment of type 2 diabetes". Expert Opinion on Therapeutic Patents 2009 Informa Healthcare for GBR LNKSD-DOI: 10.1517/13543770903153878, vol. 19, No. 10, Oct. 2009, p. 1339-1359.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
International Search Report and Written Opinion for PCT/EP2011/060449 mailed Sep. 27, 2011.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

(56) References Cited

OTHER PUBLICATIONS

Meece, J. "When Oral Agents Fail: Optimizing Insulin Therapy in the Older Adult". Consultant Pharmacist, The Society, Arlington, VA US. Vol. 24, No. Suppl B, Jun. 1, 2009, p. 11-17.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Thomas, L., "Chronic treatment with the Dipeptidyl Peptidase-4 Inhibitor BI 1356[9R)-8-(3-Amino-piperidin-1-yl)-7- but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Levien, T.L. et al, "New drugs in development for the treatment of diabetes", Diabetes Spectrum, American Diabetes Association, US, vol. 22, No. 2, Jan. 1, 2009, pp. 92-106.
He, Y. L .et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
Bastin, R.J. et al., "Salt Selection and Optimization Procedures for Pharmaceutical New Chemical Entities". Organic Process Research and Development, 2000, vol. 4, p. 427-435.
Gennaro, Alfonso R. Remington Farmacia, 2003, Spanish copy: p. 828, English copy: pp. 711-712, Preformulation, Chapter 38.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
International Search Report and Written Opinion for PCT/EP2011/070156 dated Jan. 17, 2012.
International Search Report and Written Opinion for PCT/EP2010/064691 mailed Apr. 6, 2011.
Demuth, H-U. et al., "Type 2 diabetes—Therapy with dipeptidyl peptidase IV inhibitors". Biochimica et Biophysica Acta, vol. 1751(1), 2005, p. 33-44.
Hunziker, D. et al, "Inhibitors of DPP IV-recent advances and structural views", Current Topics in Medicinal Chemistry, 2005, vol. 5 issue 16, pp. 1623-1637.
Gallwitz, B. "Sitagliptin with Metformin: Profile of a Combination for the Treatment of Type 2 Diabetes". Drugs of Today, Oct. 2007, 43(10), p. 681-689.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Kelly. T., "Fibroblast activation protein-cx and dipeptidyl peptidase IV (CD26)P: Cell-surface proteases that activate cell signaling and are potential targets for cancer therapy". Drug Resistence Update 8, 2005, vol. 8. No. 1-2, pp. 51-58.
Goldstein, L.A., et al., "Molecular cloning of seprase: a serine integral membrane protease from human melanoma." Biochimica et Biophysica Acta, vol. 1361, 1997, No. 1, pp. 11-19.
European Search Report for EP 08 15 9141 mailed Apr. 6, 2009 (European counterpart of U.S. Appl. No. 12/143,128).
International Search Report for PCT/EP03/12821 mailed Mar. 30, 2004.
International Search Report for PCT/EP03/13648 mailed Apr. 5, 2004.
International Search Report for PCT/EP2007/058181 mailed Nov. 28, 2007.
International Search Report and Written Opinion for PCT/EP2012/063852 mailed Sep. 6, 2012.
Sarafidis, P. et al., "Cardiometabolic Syndrome and Chronic Kidney Disease: What is the link?"JCMS 2006, 1: p. 58-65.
Kim, Kwang-Rok et al., "KR-62436, 6-{2-{2-(5-cyano4,5-dihydropyrazol-1-yl)-2-oxoethylamino}ethylamino}nicotinonitrile, is a novel dipeptidyl peptidase-IV (DDP-IV inhibitor with anti-hyperglycemic activity" European Journal of Pharmacology 518, 2005, p. 63-70.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Dave, Rutesh H. "Overview of pharmaceutical excipients used in tablets and capsules." Drug Topics, Oct. 24, 2008.
Abstract in English for DE10109021, 2002.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
American Diabetes Association, "Standards of Medical Care in Diabetes-2008." Diabetes Care, Jan. 2008, vol. 31, Supplement 1, pp. S12-S54.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Eucreas Scientific Discussion, 2007, p. 1-27, www.emea.europa.eu/humandocs/PD/Fs/EPAR/eucreas/H-807-en6.pdf, Anonymous.
Clinical Trials, No. NCT00622284, "Efficacy and Safety of BI 1356 in combination with metformin in patients with type 2 diabetes" 2012, pp. 1-5.
Pratley, R. et al., "Inhibition of DPP-4: a new therapeutic approach for the treatment of type 2 diabetes." Current Medical Research and Opinion, 2007, vol. 23, No. 4, pp. 919-931.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Chemical Abstracts Service, Database Accession number No. RN 668270-12-01, 2004, "1H-Purine-2,6-dione, 8-(3R)-3-amino-1-piperidinyl]-7-(2-butyn-1-yl)-3,7-dihydro-3-methyl-1-[(4-methyl-2-quinazolinyl)methyl]".
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.
Balbach, S. et al., "Pharmaceutical evaluation of early development candidates the 100 mg-approach". International Journal of Pharmaceutics, 2004, vol. 275, pp. 1-12.
Singhal, D. et al., "Drug polymorphism and dosage form design: a practical perspective." Advanced Drug Delivery Reviews, 2004, vol. 56, pp. 335-347.
Hilfiker, R. et al., "Relevance of Solid-state Properties for Pharmaceutical Products." Polymorphism in the Pharmaceutical Industry, 2006, Chapter 1, pp. 1-19.
Dunitz, J. et al., "Disappearing Polymorphs." Acc. Chem. Res. 1995, vol. 28, No. 4, pp. 193-200.

(56) References Cited

OTHER PUBLICATIONS

Byrn, Stephen R. "Solid-State Chemistry of Drugs." Academic Press, 1982, pp. 1-27.
Bernstein, Joel "Polymorphism in Molecular Crystals." Oxford University Press, 2002, p. 9.
Third Party Observation for application No. EP20070728655, May 13, 2013.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.
Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Fukushima et al., Drug for Treating Type II Diabetes (6), "action-mechanism of DPP-IV inhibitor and the availability thereof" Mebio, 2009, vol. 26, No. 8, p. 50-58.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Cotton, M.L. et al., "L-649,923—The selection of an appropriate salt form and preparation of a stable oral formulation." International Journal of Pharmaceutics, 1994, vol. 109, Issue 3, pp. 237-249.
International Search Report for PCT/EP2007/054204 mailed Mar. 8, 2007.
Lovshin, J.A. et al., "Incretin-based therapies for type 2 diabetes mellitus." Nature Reviews Endocrinology, 2009, vol. 5, pp. 262-269.
International Search Report and Written Opinion for PCT/EP2013/060312 mailed on Sep. 4, 2013.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Headland, K. et al., "The Effect of Combination Linagliptin and Voglibose on Glucose Control and Body Weight." 73rd Annual Meeting Science Session, ADA, Chicago, Jun. 21, 2013.
Nielsen, L., "Incretin Mimetics and DPP-IV Inhibitors for the Treatment of Type 2 Diabetes." Drug Discovery Today, 2005, vol. 10, No. 10, pp. 703-710.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
International Search Report and Written Opinion for PCT/EP2013/059828 mailed Aug. 6, 2013.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
Chaykovska, L. et al., "Effects of DPP-4 Inhibitors on the Heart in a Rat Model of Uremic Cardiomyopathy." www.plosone.org, 2011, vol. 6, No. 11, p. e27861.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
International Search Report and Written Opinion for PCT/EP2013/059831 mailed on Aug. 9, 2013.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013.

Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
International Search Report and Written Opinion for PCT/EP2013/060311 mailed Aug. 9, 2013.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.
International Search Report and Written Opinion for PCT/EP2013/070978 mailed on Oct. 31, 2013.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Glucophage® Prescribing Information, 2001.
Januvia Prescribing Information and Product Label, 2006.
Beauglehole, Anthony R., "N3-Substituted Xanthines as Irreversible Adenosine Receptor Antagonists." Ph.D. Thesis, Deakin University, Australia, 2000, pp. 1-168.
Janumet Prescribing Information, revised Jan. 2008.
Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.
Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.
ACTOS Prescribing Information, 1999, pp. 1-26.
EMEA: European Medicines Agency, "Galvus (vildagliptin)" Retrieved online on Jan. 21, 2016.
Novartis AG, Investor Relations Release, "Galvus, a new oral treatment for type 2 diabetes, receives positive opinion recommending European Union approval." Securities and Exchange Commission, Form 6-K, 2007, pp. 1-4.
Galvus (Vildagliptin) Scientific Discussion, EMEA, 2007, pp. 1-34.
International Search Report and Written Opinion for PCT/EP2015/074030 mailed Feb. 4, 2016.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Banker, Gilbert S., "Prodrugs." Modern Pharmaceutics Third Edition, Marcel Dekker, Inc., 1996, p. 596.
Wikipedia, "Linagliptin" Sep. 12, 2015. <https://en.wikipedia.org/w/index.php?title=Linagliptin&oldid=333469979>.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Schnapp, G. et al., "Comparative Enzyme Kinetic Analysis of the Launched DPP-4 Inhibitors." American Diabetes Association, Abstract 1048-P, 2014.
Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.
Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.
Cao, C. et al., "The clinical application of linagliptin in Asians." Therapeutics and Clinical Risk Management, 2015, vol. 11, pp. 1409-1419.

(56) References Cited

OTHER PUBLICATIONS

Januvia, 25mg, 50mg, 100 mg, Summary of Product Characteristics, 2015, www.medicines.org.uk/EMC <http://www.medicines.org.uk/EMC>.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Rosenstock, J. et al., "Triple Therapy in Type 2 Diabetes." Diabetes Care, 2006, vol. 29, No. 3, pp. 554-559.
Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.
EMEA Guidelines on Galvus®, 2007, pp. 1-34.
EMEA Guidelines on Eucreas®, 2007, pp. 1-27.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
U.S. Appl. No. 15/235,575, filed Aug. 12, 2016, Inventor: Klaus Dugi. (MPEP 609.04(a)(II)(C)).
Kishore, Preeti MD., "Complications of Diabetes Mellitus." Merck Manual Consumer Version, 2016, pp. 1-7.
Fantus, George, "Metformin's contraindications: needed for now." Canadian Medical Association Journal, 2005, vol. 173, No. 5, pp. 505-507.
EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.
Jibiinkoka-Tenbo, Vision of Otorhinolaryngology, How to use antimicrobial drug in a patient with impairment of renal function, vol. 44, No. 3, 2001, p. 217-220.
Rinsho-Yakuri, Jpn. J. Clin. Pharmacol. Ther. Pharmacokinetics: excretion, 30(3) 1999. 2 pages.
Fiorucci, et al. Trends in Molecular Medicine, Targeting farnesoid X receptor for liver and metabolic disorders, 13(7), 2007, p. 298-309.
Morhenn, "Keratinacyte proliferation n wound healing and skin diseases", Immunology Today, vol. 9, Issue 4, 1988, p. 104.
Karaliede et al, Diabetes Care, Endothelial Factors and Diabetic Nephropathy, 2011, 34, Suppl 2, p. 291-296.
Hansen, European Journal of Pharmacology, "The DPP-IV inhibitor linagliptin and GLP-1 induce synergistic effects on body weight loss and appetite suppression in the diet-induced obese rat", 2014, p. 254-263.
Diabetes, Type 1 Diabetes-Associated Autoantibodies, 2009, vol. 52, Issue 8, p. 675-677.
Merck manual, 18th Edition, published Apr. 25, 2007, p. 594-598, Japanese Edition.
Scientific Discussion on Sifrol, EMEA, 2005, p. 1-9.
Scientific Discussion for Sifrol, European Public Assessment Reports, 2005, p. 1.
The Textbook of Pharmaceutics, Pharmaceutical Subcommitee Hanrimwon, 2005, p. 1-6.
Mettler Toledo "interpreting DSC curves Part 1: Dynamic Measurements" Jan. 2000. Available from www.masointechnology.ie.x/Usercom_11.pdf, 28 pages.
Brittain, Polymorphism on Pharmaceutical Solids, Chapter 5 Generation of Polymorphs, vol. 95, 1999, p. 183-226.
Luo, Theory and Practice of Modern Physical Pharmacy, Shangai Scientific And Technical Literature Publishing House, 2005, p. 294.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Kim, Comparison of DPP-4 Inhibitors, The Journal of Korean Diabetes, http:dx.doi.org/10.4093/jkd.2013.14.3.111. 6 pages.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Abstract in English for JP 2002/348279, Dec. 4, 2002.
Abstract in English for JP 2003/286287, Oct. 10, 2003.
Holman, et al., "Addition of biphasic, prandial, or basal insulin to oral therapy in type 2 diabetes", N. England Journal Medicine, p. 1716-1730, 2007.
Gomez-Perez, et al, "Insulin Therapy:current alternatives", Arch. Med.Res. 36: p. 258-272 (2005).
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Lee Jones, K. et al., "Effect of Metformin in Pediatric Patients With Type 2 Diabetes." Diabetes Care, 2002, vol. 25, No. 1, pp. 89-94.
Glucotrol XL (glipizide), package insert, Pfizer, Apr. 1, 2002.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Thornber, C.W., "Isosterism and Molecular Modification in Drug Design." Chemical Society Reviews, 1979, pp. 563-580.
Chemgaroo, "Leaving Group." 1999, Retrieved online: http://www.chemgapedia.de/vsengine/vlu/vsc/en/ch/12/oc/vluorganik/substitution/sn_2/sn2.vlu/Page/vsc/en/ch/12/oc/substitution/sn_2/abgangsgrupen/abgangsgruppe.vscml.html.
Silverman, G. et al., "Handbook of Grignard Reagents." 1996, Retrieved online: <http://books.google.com/books?d=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.
John Hopkins Children's Center, "Liver Disorders and Diseases." Retrieved online May 26, 2014 <http://www.hopkinschildrens.org/non-alcoholic-fatty-liver-disease.aspx>.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Sortino, M.A. et al., "Linagliptin: a thorough characterization beyond its clinical efficacy." Frontiers in Endocrinology, 2013, vol. 4, Article 16, pp. 1-9.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.

(56) References Cited

OTHER PUBLICATIONS

Haluzik, M. et al., "Renal Effects of DPP-4 Inhibitors: A Focus on Microalbuminuria." International Journal of Endocrinology, 2013, vol. 35, No. 6, pp. 1-7.
International Search Report and Written Opinion for PCT/EP2012/077024 mailed Feb. 19, 2013.
Rosenbloom, et al., "Type 2 Diabetes mellitus in the child and adolescent", Pediatric Diabetes, 2008, p. 512-526.
International Search Report for PCT/EP2013/060309 mailed Aug. 9, 2013.
International Search Report and Written Opinion for PCT/EP2014/055113 mailed May 16, 2014.
Iwamoto, Yasuhiko, "Insulin Glargine." Nippon Rinsho, 2002, vol. 60, Suppl. 9, pp. 503-515.
Prescribing Information, Package insert for Leprinton tablets 100mg, Manufacturer: Tatsumi Kagaku Co., Ltd., Mar. 2003, pp. 1-3.
Hashida, Mitsuru, "Strategies for designing and developing oral administration formulations." Yakuji-Jiho, Inc., 1995, pp. 50-51 and 89.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
International Search Report and Written Opinion for PCT/EP2014/062398 mailed Aug. 20, 2014.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Rask-Madsen, C. et al., "Podocytes lose their footing." Nature, 2010, vol. 468, pp. 42-44.
International Search Report for PCT/EP2013/070979 mailed Nov. 26, 2013.
McNay, David E.G. et al., "High fat diet causes rebound weight gain." Molecular Metabolism, 2013, vol. 2, pp. 103-108.
Radermecker, Regis et al., "Lipodystrophy Reactions to Insulin." American Journal of Clinical Dermatology, 2007, vol. 8, pp. 21-28.
Sheperd, Todd M. et al., "Efective management of obesity." The Journal of Family Practice, 2003, vol. 52, No. 1, pp. 34-42.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
Pearson, E. R. et al., "Variation in TCF7L2 Influences Therapeutic Response to Sulfonylureas." Diabetes, 2007, vol. 56, pp. 2178-2182.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L .et al., "Transcription Factor 7-Like 2 Regulates B-Cell Survival and Function in Human Pancreatic Islets." Diabetes, 2008, vol. 57, pp. 645-653.
Zimdahl, H. et al., "Influence of TCF7L2 gene variants on the therapeutic response to the dipeptidylpeptidase-4 Inhibitor linagliptin." Diabetologia, 2014, vol. 57, pp. 1869-1875.

Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Tadayyon, M. et al., "Insulin sensitisation in the treatment of Type 2 diabetes." Expert Opinion Investigative Drugs, 2003, vol. 12, No. 3, pp. 307-324.
Hocher, B. et al., "The novel DPP-4 inhibitors linagliptin and BI 14361 reduce infarct size after myocardial ischemia/ reperfusion in rats." International Journal of Cardiology, 2013, vol. 167, pp. 87-93.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Klein, T. et al., "Linagliptin alleviates hepatic steatosis and inflammation in a mouse model of non-alcoholic steatohepatitis." Medical Molecular Morphology, 2014, vol. 47, pp. 137-149.
Standl, E. et al., "Diabetes and the Heart." Diabetes Guidelines (DDG), 2002, pp. 1-25.
National Program for Care Guidelines, "Type 2 Diabetes mellitus." 2002, First Edition, pp. 1-50.
Drucker, Daniel J., "Dipeptidyl Peptidase-4 Inhibition and the Treatment of Type 2 Diabetes." Diabetes Care, 2007, vol. 30, No. 6, pp. 1335-1343.
Schillinger, M. et al., "Restenosis after percutaneous angioplasty: the role of vascular inflammation." Vascular Health and Risk Management, 2005, vol. 1, No. 1, pp. 73-78.
Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Gupta, V. et al., "Choosing a Gliptin." Indian Journal of Endocrinology and Metabolism, 2011, vol. 15, No. 4, pp. 298-308.
Linagliptin Monograph, Published by VACO PBM-SHG US Veteran's Administration, 2011, pp. 1-17.
International Search Report and Written Opinion for PCT/EP2013/054524 mailed on Apr. 24, 2013.
International Search Report and Written Opinion for PCT/EP2012/053910 mailed May 14, 2012.
Merck Manual of Diagnosis and Therapy: "Obesity." 1999, 17th Edition, Chapter 5, pp. 58-62.
International Search Report for PCT/EP2014/060160 mailed Nov. 8, 2014.
Abstract for AU 2003280680, Jun. 18, 2004.
Abstract for AU 2009224546, Sep. 17, 2009.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Abstract in English for DE19705233, Aug. 13, 1998.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Gall, "Prevalence of micro-and macroalbuminuria, arterial hypertension, retinopathy and large vessel disease in European type 2 (non-insulin dependent) diabetic patients", Diabetologia (1991) 655-661.
Clinical Trial, NCT00622284, clinicaltrials.gov, updated Feb. 22, 2008.
Clinical Trials NCT00601250, clinicaltrials.gov, Jan. 25, 2008.
Halimi, "Combination treatment in the management of type 2 diabetes: focus on vildagliptin and metformin as a single tablet", Vascular Health and Risk Management, 2008 481-92.
Colorcon, "Lactose Replacement with Starch 1500 in a Direct Compression Formula." 2005, pp. 1-4.
Lachman, L. et al., "The Theory and Practice of Industrial Pharmacy." Varghese Publishing House, Third Edition, 1987, pp. 190-194.

(56) References Cited

OTHER PUBLICATIONS

Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.
Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.
Vincent, S.H. et al., "Metabolism And Excretion of the Dipeptidyl Peptidase 4 Inhibitor [14C]Sitagliptin in Humans." Drug Metabolism And Disposition, 2007, vol. 35, No. 4, pp. 533-538.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.
Yap, W.S. et al., "Review of management of type 2 diabetes mellitus." Journal of Clinical Pharmacy and Therapeutics, 1998, vol. 23, pp. 457-465.
Flatt, P.R. et al., "Dipeptidyl peptidase IV (DPP IV) and related molecules in type 2 diabetes." Frontiers in Bioscience, 2008, vol. 13, pp. 3648-3660.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.
Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.
Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Pietruck, F. et al., "Rosiglitazone is a safe and effective treatment option of new-onset diabetes mellitus after renal transplantation." Transplant International, 2005, vol. 18, pp. 483-486.
Hinnen, D. et al., "Incretin Mimetics and DPP-IV Inhibitors: New Paradigms for the Treatment of Type 2 Diabetes." Journal Of The American Board Of Family Medicine, 2006, vol. 19, No. 6, pp. 612-620.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Lindsay, J.R. et al., "Inhibition of dipeptidyl peptidase IV activity by oral metformin in Type 2 diabetes." Diabetic Medicine, 2005, vol. 22, pp. 654-657.
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.
Inzucchi, Silvio E., "Oral Antihyperglycemic Therapy for Type 2 Diabetes." The Journal of the American Medical Association, 2002, vol. 287, No. 3, pp. 360-372.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.

Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Gwaltney, S.L. II et al., "Inhibitors of Dipeptidyl Peptidase 4." Annual Reports In Medicinal Chemistry, 2005, vol. 40, pp. 149-165.
Sulkin, T.V. et al., "Contraindications to Metformin Therapy in Patients With NIDDM." Diabetes Care, 1997, vol. 20, No. 6, pp. 925-928.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Kirpichnikov, D. et al., "Metformin: An Update." Annals of Internal Medicine, 2002, vol. 137, No. 1, pp. 25-33.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Canadian Diabetes Association, "Pharmacologic Management of Type 2 Diabetes." Canadian Journal of Diabetes, 2003, vol. 27, Suppl. 2, pp. S37-S42.
American Association of Clinical Endocrinologists, "Medical Guidelines for Clinical Practice for the Management of Diabetes Mellitus." Endocrine Practice, 2007, col. 13, Suppl. 1, pp. 1-68.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.
Wang, Y. et al., "BI-1356. Dipeptidyl-Peptidase IV Inhibitor, Antidiabetic Agent." Drugs of the Future, 2008, vol. 33, No. 6, pp. 473-477.
Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
International Search Report for PCT/EP2005/001427 mailed May 23, 2005.
International Search Report and Written Opinion for PCT/EP2006/064657 mailed Nov. 2, 2006.
International Search Report for PCT/EP2008/060738 mailed Nov. 5, 2008.
International Search Report and Written Opinion for PCT/EP2009/053978 mailed Sep. 29, 2009.
International Search Report and Written Opinion for PCT/EP2009/056722 mailed Aug. 13, 2009.
International Search Report for PCT/EP2009/060170 mailed Oct. 28, 2009.
International Search Report for PCT/EP2002/01820 mailed May 7, 2002.
World Health Organization (WHO). "Addendum 1 to "The use of stems in the selection of International Nonproprietary hames (INN) for pharmaceutical substances"" Online Jun. 19, 2007, pp. 1-3, retrieved from URL: http://www.who.int/medicindedocs/index/assoc/s1414e/s1414e.pdf.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Clinical Trials. NCTO622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Balaban, Y.H.et al., "Dipeptidyl peptidase IV (DDP IV) in NASH patients" Annals of Hepatology, vol. 6, No. 4, Oct. 1, 2007, pp. 242-250, abstract.

(56) References Cited

OTHER PUBLICATIONS

He, Y.L. et al., "The influence of hepatic impariment on the pharmacokinetics f the dipeptidyl peptidase IV (DPP-4) Inhibitor vildagliptin" European Journal of Clinical Pharmacology, vol. 63, No. 7, May 8, 2007, p. 677-686.
Mendes, F.D, et al. "Recent advances in the treatment of non-alcoholic fatty liver disease". Expert Opinion on Investigational Drugs, vol. 14, No. 1, Jan. 1, 2005, p. 29-35.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
White, John R. Jr., "Dipeptidyl Peptidase-IV Inhibitors: Phamacological Profile and Clinical Use". Clinical Diabetes, Apr. 2008, vol. 26, No. 2, pp. 53-57.
Stahl, P.H., "Handbook of Pharmaceutical Salts" C.G. Wermuth, Wiley-VCH, 2002, pp. 1-374.
Chemical Abstract. EP412358, 1991:185517, Findeisen.
Chemical Abstract: FR2707641, 1995:543545, Dodey.
Wikipedia, Annulation. Jun. 23, 2008, http://en.wikipedia.org/wiki/Annelation.
March, J. "Advanced Organic Chemistry: Reactions, Mechanisms, and Structure". Fourth Edition, 1992, pp. 652-653.
Abstract in English for DE2205815, 1972.
Abstract in English for EP0023032, 1981.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Gallwitz, B. et al., "Saxagliptin, a dipeptidyl peptidase IV inhibitor for the treatment of type 2 diabetes". Idrugs, vol. 11, No. 12, Dec. 2008, p. 906-917.
Gwaltney, S. "Medicinal Chemistry Approaches to the Inhibition of Dipeptidyl Peptidase IV", Current Topics in Medicinal Chemistry, 2008, 8, p. 1545-1552.
International Search Report for PCT/EP2003/12821 mailed Mar. 30, 2004.
International Search Report for PCT/EP2003/13648 mailed Apr. 5, 2004.
International Search Report and Written Opinion for PCT/EP2010/051817 dated Jun. 8, 2010.
Abstract in English for KR20070111099, Nov. 11, 2007.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Deacon, C.F., et al. Inhibitors of dipeptidyl peptidase IV: a novel approach for the prevention and treatment of Type 2 diabetes? Expert Opinion on Investigational Drugs, 2004, September, vol. 13, No. 9, p. 1091-1102.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Conarello, S.L. et al., "Mice lacking dipeptidyl peptidase IV are protected against obesity and insulin resistance". PNAS, May 27, 2003, vol. 100, No. 11, p. 6825-6830.
Aulinger, B.A. et al., "Ex-4 and the DPP-IV Inhibitor Vildagliptin have Additive Effects to Suppress Food Intake in Rodents". Abstract No. 1545-P, 2008.
Schwartz, M. S. et al., "Type 2 Diabetes Mellitus in Childhood: Obesity and Insulin Resistance". JAOA Review Article, vol. 108, No. 9, Sep. 2008, p. 518.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
International Search Report—European Search Report for PCT/EP2003/09127 mailed Mar. 1, 2011.
Chemical Abstracts Accession No. 106:95577 Romanenko et al., "Synthesis and Biological Activity of 3-Methyl, 7-or 8-alkyl-7,8dialkyl, heterocyclic, and cyclohexylaminoxanthines," Zaporozh. Med. Institute (1986).
International Search Report and Written Opinion for PCT/EP2009/060521 mailed Mar. 9, 2010.
Zhang, Classification and Treatment Prinicples of Diabetes, Beijing Medical Univ and China Union Medical Univ. Joint Publishing House. 1st ed., 1998, p. 939.
Diabetes and Foot ulcers, www.diabetes.co.uk/diabetes-complications/diabetic-foot-ulcers.html, 2018.
Aronow, Congestive Heart Failure, Treatment of Heart Failure in Older Persons with Coexisting Conditions, vol. 9, No. 3, 2003, p. 142-147.
Tiwari, Linagliptin, A dipeptyl peptidase-4 inhibitor for the treatment of type 2 diabetes, Current Opinion in Ivestigational Drugs, vol. 10, 2009, p. 1091-1104.
Isomaa, Chronic Comlications in patients with slowly progressing atutoimmune type 1 diabetes, Diabetes Care, vol. 22, 1999, p. 1347-1353.
Seijin-Byou, The Journal of Adult Diseases, 2008, vol. 38, p. 438-444., abstract attached.
Fuguchi, Therapeutic Effects and Adverse Reactions to Oral Hypoglycemic Agents, Journal of the Nippon Hospital Pharmacists Assoc, 1976, vol. 1, p. 226-229, abstract only.
Colorcon (retrieved from website http://www.colorcon.com/products-formulation/all-products/film-coatings/immediate-release/opadry, published2015).
Bergmann, Decrease of serum dipeptidylpeptidase activity in severs sepsis patients, Clinica Chimica Acta 2002., p. 123-126.
Groop, Effects of The DPP-4inhibitor linagliptin on albuminuria in patients with type 2 diabetes, www.abstractsonline.com, 2013, 1 page.
Clinical Journal of Chinese Medicine, vol. 3, 2008, p. 360-364.
Clinical Trials.gov, Efficacy and Safety of Lingliptin in Elderly Patients with Type 2 Diabetes, Mar. 10, 2010, NCT01084005.

(56) References Cited

OTHER PUBLICATIONS

Barrara, Granulation, Handbook of Powder Technology, vol. 11, 2015, 2 pages.
Clinical Trials.gov, NCT00622284, Efficacy and Safety of BI 1356 in Combination with Metformin in Patients with Type 2 Diabetes, 2013.
Kleeman, Pharmaceutical Substances, Synthesesm Patents, Applications, p. 1196-1997, 1999.
Clinical Trials.gov, Efficacy and Safety of BI 1356 in Combination with Metformin in Patients with Type 2 Diabetes, NCT00309608, 2006.
Clinical Trials.gov, 52-week add-on to metformin comparison of saxagliptin and sulphonurea, NCT00575588, 2007.
Stahl, Handbook of Pharmaceutical Salts, Properties, Selection and Use, 2002.
Janumet dosing instructions, Highlights of Prescribing information, 2008.
Ennis, Handbook of Pharmaceutical Granulation Technology, Theory of Granulation, 2010.
Houben-Weyl, Oxygen Compounds, Methods of Organic Chemistry, 1929, 5 pages.
Blotta, On Biguanides, Chem. Institute at the Univ. of Wroclaw, vol. 62, 1929.
Mojsov, Insulintropin: Glucagin like peptide: Lab of Molecular Endocrinology, vol. 79, 1987, p. 616-619.
Holst, Role on incretin hormones in the regulation of insulin, Am j. Physiol Endocrinol Metab., 2004.
Matsuyama, Glucagen like peptide: a ptotent glucagonostatic hormone, Diabetes Research, 1988, p. 281-288.
Drug Data Report, 1994, Source, Smith Kline Beechman, Treatments for Septic Shock, p. 459.
Horie, Biomedcentral, Design, statistical analysis and sample size calculation of a phase IIb/III study of linagliptin vs. voglibose and placebo, 2009.
International Search report for PCT/EP2019/069126, mailed Oct. 2, 2019.
Press, Synthesis of 5,6 Dimethoxyquinazolin-2(1-H) ones, J. Heterocyclic Chwm, 1986.
Adams, Pub Pharmafile, 2011, Boehringer-lilly launch diabetes drug tradjenta in US.
Excerpt from Orange Book of Product Tradjenta, Feb. 5, 2011.
Publication Boehringer Ingelheim and Lilly's New type 2 Diabetes Treatment tradjenta, 2015, p. 1-7.
Smithies, The Jackson Lab, Mouse Strain Datasheet, 2019, p. 1-2.
Who drug information, International nonproprietary Names for Pharmaceutical Substances, vol. 23, 2009, 1 page.
Pradham, Wound-healing abnormalities in Diabetes, Dept. of surgertm Harvard, Touch Briefings, 2007.
Basi, Diabetes Care, vol. 31, 2008, 1 page.
Sampanis, Hippokratia, Management of Hyperglcemia in patients with diabetes mellitus and chronic renal failure, vol. 12, p. 22-27, 2008.
US Court of Appeals for the Federal Circuit, *Boehringer Ingelheim Pharmaceuticals, Inc.* v. *Mylan Pharmaceuticals, Inc.*, Decided Mar. 16, 2020, retrieved online http;///www.cafc.uscourts.gov/sites/default/files/opinions-orders/19-1172.Opinion.3-16-2020_1551193.pdf (last visited May 29, 2020.).
Ahren, Vascular Health and Risk Management, Novel combination treatment of type 2 diabetes DPP-4 inhibition plus metformin, 2008, p. 383-394.
Linagliptin, Pub Chem, Clinical Trial Search of Japan, https://pubchem.ncbi.nlm.nih.gov/compound/10096344 dated Jun. 25, 2020.
Aschner, Emerging Treatments and Technologies, Effect of the Dipepttidyl Peptidase-4 Inhibitor Sitagliptin as Monotherapy on Glycemic Control in Patients with Type 2 Diabetes, vol. 29, 2006.
Huettner, Diabetes, Novel and Selective Xanthine, Jun. 2007 Supplement vol. 56.
Heizmann, Xanthines as scaffold for molecular diversity, Molecular diversity, vol. 2, 1996, p. 171-174.
Hanrinwon, Pharmaceutical Subcommittee, Pharmaceutics, p. 284-288, 1995.
Schafer, Impaired glucagen like peptide 1 induced insulin secretions in carriers of transcription, Diabetologica, vol. 50, 2007.
Encyclopedia of Pharma Technology, Swarbrick, 3rd Ed., vol. 1, Absorption of Solid Surfaces, 2007.
Clinical Trials, NCT006002472, BI 1356 In combination with Metformin submitted Feb. 27, 2014.
Boehringer Ingelheim Press Release: Boehringer Ingelheim's diabetes Pipeline continues to advance as the company announces conclusion of robust Phase III pivotal trials programme for linalgiptin, Small Molecules, Published Sep. 28, 2009, 2 pages.
Nationale Versorgungs-Leitlinie, Diabetes Mellitus, 2004.
Kibbe, Handbook of Pharmaceutical Excipients, 3rd Edition, 2009, p. 104-107.
Wade, Organic Chem, 6th Edition, 2006, p. 918, 943-956.
News Article, https:/www.in-phamratechnologist.com-Article-France-and-maerck-say-reformulated-Euthyrox-is-safe.)—Sep. 17, 2017, 1 page.
Brosius, Mouse Models of Diabetic Neuropathy, JASN, vol. 20, 2009, 5 pages.
Schmeider, Telmisartan in incipient and overt renal disease, J. Nephrol, vol. 24, 2011, 10 pages.
Stedman's Medical Dictionary, 27th edition, Def. of nephropathy, 1999, 1 page.
Clarivate Analytics on STN: Confirmation of the public accessibility of Schmeider before May 31, 2011.
Anonymous, New England Journal of Medicine, The effect of intensive treatment of diabetes on the development and brogession of long term complicationsin insulin dependent mellitus, vol. 329, 1993.
Hanrimwon, Pharmaceutics Subcommitee, 2000, p. 321-322.
Eckhardt, 8-(3-(R)-Aminopiperidin-1-yl)-7-but-2-ynyl-3-methyl-1-(4-methyl-quinazolin-2-ylmethyl)-3,7-dihydropurine-2,6-dione (BO1356), Journal of Medicinal Chem., vol. 50, 2007, p. 6450-5453.
Rabinovitch, Thyophylline protects against diabetes in BB rats, Diabetologica, vol. 33, 1990.
International Search Report for PCT/EP2019/069131 mailed Oct. 8, 2019.
Clinical Trials.gov, for BI1356 for Patients in Combination wtih Metormin in Patients with Type 2 Diabetes.2014.
Bell, Diabetes Care, The frequent, forgotten, and and often fatal complication of diabetes, vol. 26, 2003, 9 pages.
International Search Report for PCT/EP2019/EP069131 mailed Jan. 28, 2021.
Isoda, Certificate of experimental Results, Analytical Research Development, 2021.
Luo, Shanghai Scientific and Technical Lit Publishing House, Theory and Practice of Modern Physical Pharmacy, vol. 4, 2005, p. 294.
Forst, ADA, Novel, Potent, Selective, DPP-4 inhibitor BI 1356 Significantly lowers HbA1c after only 4 weeks of treatment, 2007.
The 4th Edition, Experimental Chem., Course 1, Society of Japan, 1990, p. 184-186.
Snyder, Use of Insulin and Oral hypoglycemic medication in patients with diabetes mellitus and advanced kidney disease, Diabetic Medication in Kidney Disease, Seminars in Dialysis, vol. 17, 2004, p. 365-370.
Xie, Hypoglycemic Drugs, New Practical Pharmacy, 2007, p. 832-934.
Akiyama, Sulphostin, a potent Inhibitor for dipeptiyl peptidase IV, The Journal of Antibiotics, vol. 54, No. 9, 2001, p. 744-746.
Artunc, Expert opinion relating to Euro patent Ep2640371, May 11, 2022, 5 pages.
Wong, Endothelial Dysfunction, J. Cardiovasc Pharmacol, vol. 55, 2010, 8 pages.
Groop, Linagliptin and its effects on hyperglycemia, Diabetes and obes Metab vol. 10, 2017, 10 pages.
Wang, A modest decease in endothelial NOS in mice, PNAS vol. 108, 2011, 7 pages.
Du, Hyperglycemia inhibits endothelial nitric oxide synthase oxide activity, JCI, vol. 108, 2001, 9 pages.

(56) References Cited

OTHER PUBLICATIONS

Craven, Impaired nitric oxide release by glomeruli from diabetic rats, Metabolism, vol. 44, 1995, 4 pages.
Excerpts of Diabetologie in Klinik and Praxis, 5th Edition, 2003, pp. 384 and 434.
Japanese Society Of Nephrology, Clinical Practice Guidebook, 2012, 145 pages.
Lee, Common foot diseases that primary care physicians should know about, Korean Journal of Family Medicine, vol. 26, 2005, p. 127-137.
Product information for Digosin Tab, CJ Health Care, 2014, 1 page.
Lee, Radical Approach to Diabetic Neuropathy, Kidney International, vol. 72, 2007, p. 67-70.
Rungby, inhibition of dipeptidyl peptidase 4 by BI 1356, a new drug for the treatment of beta cell failure in type 2 diabetes, Expert Opin. Invest. Drugs, vol. 18, 2009, p. 835-838.
Hahr, Management of diabetes mellitus in patients with chronic kidney disease, Clinical Diabetes and Endocrinology, vol. 10, 2015, 9 pages.
Duong, Population pharmacokinetics of metformin in healthy subjects and patients with type 2 diabetes, Clinical Pharmacokinetics, vol. 52, 2013, p. 373.
Bell, Prescribing for older people with chronic renal impairment, Australian Family Physician, vol. 42, 2013, 5 pages.
Munar, Drug dosing adjustments in patients with chronic kidney disease, AFP, vol. 75, 2007, 10 pages.
Laasko, Hyperglycemia and Cardiovascular Disease in Type 2 Diabetes, Diabetes, vol. 48, 1999, 6 pages.
Haffner, Mortality from coronary heart disease in subjects with type 2 diabetes and in nondiabetic subjects with and without prior myocardial infarction, The N.E. J. of Medicine, vol. 339, 1996, 6 pages.
Calles, Type 2 diabetes, Coronary Artery Disease, vol. 10, 1999, 8 pages.
Marks, Cardiovascular Risk in Diabetes, Journal of Diabetes and the complications, vol. 14, 2000, 8 pages.
Fadini, DPP-4 inhibition has no cute affect on BNP and its N-terminal pro-hormone measured by commercial immune assays, Cardiovascualr Diabetology, vol. 16, 2017, 7 pages.
Mu, Impact of DPP-4 inhibitors on plasma levels of BNP and NT-pro-BNP in type 2 diabetes mellitus, Diabetology, vol. 14, 2022, 9 pages.
McGuire, Linagliptin effects on heart failure and related outcomes in individuals with type 2 diabetes mellitus, http://shjajournals.org on Mar. 18, 2023, 11 pages.
Clifton, Do dipeptidyl Peptidase IV inhibitors cause heart failure?, Clinical therapeutics, vol. 36, 2014, 8 pages.
Shiraki, The DPP4 inhibitor linagliptin exacerbated heart failure due to energy deficiency, Pharmcology and Pharmacotherapy, downloaded from http://academic.cup.com/eurheartj/article/43/supplement_2/ehcac544268/26746435 Mar. 18, 2023.
Mu, Impact of DPP-4 inhibitors on plasma levels of BNP and NT-pro-BNP in type 2 diabetes mellitus, Diabetology and Diabetes Mellitus, vol. 14, 2022, 9 pages.
Holt, Textbook of Diabetes, 4th Ed., 2010, 48 pages.
Lee, Recent advances in the treatment of diabetes mellitus, Korean J. of Medicine, vol. 57, 1999, p. 836-848.
The Japan Diabetes Society, Practice Guidelines of Diabetes based on Scientific basis, May 25, 2004, p. 5-19, p. 37-56, p. 67-80, p. 93-121, p. 131-153.

\* cited by examiner

USE OF A DPP-4 INHIBITOR IN SIRS AND/OR SEPSIS

SEQUENCE LISTING

The instant application contains a Sequence Listing which has been submitted electronically in ASCII format and is hereby incorporated by reference in its entirety. Said ASCII copy, created on Jul. 7, 2022, is named 01-2816-US-3_SL.txt and is 601 bytes in size.

FIELD OF THE INVENTION

The present invention relates to a certain DPP-4 inhibitor (preferably linagliptin, optionally in combination with one or more other active agents) for use in treating, preventing and/or reducing the risk or likelihood of systemic inflammatory response syndrome (SIRS) and/or sepsis (SIRS/sepsis) and/or diseases related or associated therewith, to pharmaceutical compositions and combinations comprising such active components, and to certain therapeutic uses thereof.

Further, the present invention relates a certain DPP-4 inhibitor (preferably linagliptin, optionally in combination with one or more other active agents) for use in treating, preventing and/or and/or reducing the risk of SIRS/sepsis, which is one or more selected from septic or non-septic SIRS, severe SIRS/sepsis, SIRS/septic shock and multi-organ failure associated with SIRS/sepsis.

Further, the present invention relates a certain DPP-4 inhibitor (preferably linagliptin, optionally in combination with one or more other active agents) for use in treating and/or preventing metabolic diseases, particularly diabetes, especially type 2 diabetes mellitus, and/or conditions related thereto (e.g. diabetic complications), in a patient (particularly human patient) with or at risk of systemic inflammatory response syndrome (SIRS) and/or sepsis (SIRS/sepsis).

Further, the present invention relates to a method of treating, preventing and/or reducing the likelihood or risk of systemic inflammatory response syndrome (SIRS) and/or sepsis (SIRS/sepsis) in a patient (particularly human patient) in need thereof, comprising administering an effective amount of a certain DPP-4 inhibitor (preferably linagliptin), optionally in combination with one or more other active agents, to the patient.

BACKGROUND OF THE INVENTION

Systemic inflammatory response syndrome (SIRS) is an inflammatory and extreme endogenous immune response of the subject often to the presence of micro-organisms. Sepsis is defined as the presence of infection in association with SIRS. The nature of the interactions between the microbial pathogen and the host is complex and, at the tissues, results in excessive inflammation or immunosuppression, abnormal coagulation and blood flow, and microcirculatory dysfunction leading to organ injury and cell death.

Metabolic and immune system are closely involved in such inflammatory response and significantly contribute to the pathology seen. Patients with SIRS/sepsis are hyper-metabolic.

SIRS may be generally manifested as a combination of vital sign abnormalities including fever or hypothermia, tachycardia, tachypnea, and leukocytosis or leukopenia, and may be defined by two or more of the following variables:

Fever of more than 38° C. (100.4° F.) or less than 36° C. (96.8° F.)

Heart rate of more than 90 beats per minute (in absence of intrinsic heart disease)

Respiratory rate of more than 20 breaths per minute or arterial carbon dioxide tension ($PaCO_2$) of less than 32 mm Hg Abnormal white blood cell count (>12,000/μL or <4,000/μL or >10% immature neutrophils [band forms])

SIRS is nonspecific and can be caused by ischemia, inflammation, trauma, burns, infection, pancreatitis, stress, organ injury, major surgery, fractures, or several insults combined. Thus, SIRS is not always related to infection.

Clinically, SIRS/sepsis may include, be associated or complicated with hypotension, perfusion abnormalitiers, hypoperfusion, lacto-acidosis, pulmonary embolism, oliguria, organ dysfunction and/or end-organ failure (such as e.g. cardiovascular, neurologic, renal, hepatic, hematologic and/or respiratory).

The range of classifications of sepsis includes septic SIRS, severe sepsis, septic shock and multi-organ failure.

In more detail, severe SIRS/sepsis typically relates to SIRS/sepsis associated or complicated with organ dysfunction, hypoperfusion or hypotension. Hypoperfusion or perfusion abnormalities may include, but are not limited to, lactic acidosis, oliguria, or an acute alteration in mental status (e.g. polyneuropathy).

Severe sepsis may be accompanied by signs of failure of at least one organ. Cardiovascular failure is typically manifested by hypotension, respiratory failure by hypoxemia, renal failure by oliguria, and hematologic failure by coagulapathy.

SIRS/septic shock is a subset of severe SIRS/sepsis and may be defined as SIRS/sepsis induced hypotension despite adequate fluid resuscitation along or complicated with the presence of perfusion abnormalities that may include, but are not limited to, lactic acidosis, oliguria, or an acute alteration in mental status (e.g. polyneuropathy).

Multi-organ failure (MODS, multiple organ dysfunction syndrome) is the presence of altered organ function in an acutely ill patient such that homeostasis can not be maintained without intervention. The following organ systems may be affected by MODS as a complication associated with SIRS/sepsis: cardio- and/or cerebrovascular system, lung, kidney, liver, brain, heart, coagulation system, and/or gastrointestinal tract.

SIRS/sepsis within the meaning of this invention include at least one of (septic or non-septic) SIRS, severe SIRS/sepsis, SIRS/septic shock and/or multi-organ failure associated with SIRS/sepsis.

The mortality of sepsis is high with 25% over 5 years and up to 80% in those patients developing multi organ failure. The mortality rate in septic diabetes patients is significantly higher than in septic non-diabetes patients.

Although the dysfunctional events that lead to septic shock involve multiple biologic systems, immune response remains central to the development of septic shock. This immune response is often initiated by innate immune cells system (i.e., macrophages, neutrophils, NK cells) recognizing microbial products through a set of receptors known as pattern recognition receptors (PRRs) that can recognize a pathogen-associated molecular patterns or a micro-associated molecular pattern (such as lipopolysaccharide, LPS). For instance Toll-like receptors (TLRs) activation by LPS triggers intercelluar signaling and activation of transcriptional factors such as NFkB which in turn activates proinflammatory cytokines, chemokines, coagulations factors and proteases. It was also shown that the innate immune response can be dramatically influenced by the cellular redox state, and thus a better understanding of oxidative regulation of innate immunity could lead to new treatments for sepsis. On the other hand, patients suffering from sepsis in a later status consistenly show a decline in their immune responsiveness (immune deficiency of the adaptive immune system). In particular, the immunological status is typisized by leukocytes producing increased levels of anti-inflammatory cytokines such as IL-10 and exhibit T cell anergy sometimes associated with a shift in the Th cell pattern to a predominant Th2 response.

Risk factors for SIRS and sepsis may include, without being limited to, for example higher age (e.g. 60-80 years or >80 years), renal insufficiency (e.g. chronic or acute renal failure or nephropathy), wound healing disturbances, and/or diabetes mellitus, particularly associated with diabetic foot or ulcer, or diabetic wound infection.

Further, the frequency of infections, such as urinary tract infections, respiratory infections, wound infections, gastro-intestinal infections, cholecystitis, necrotizing fasceitis, foot ulcers, AIDS and hepatitis can typically be higher in diabetes than non-diabetes patients.

Therefore, it is expected that the prevalence of sepsis is higher in diabetic patients than non-diabetics, and diabetes patients are expected to be at an increased risk of sepsis compared to non-diabetes patients and the risk may be even higher with aging and/or other underlying diseases, such as impaired renal function (e.g. renal failure, nephropathy), wound healing disturbances, impaired liver function (e.g. cirrhosis), immune deficiency and/or malignancies.

SUMMARY OF THE INVENTION

The present invention relates to a certain DPP-4 inhibitor (preferably linagliptin, optionally in combination with one or more other active agents) for use in treating, preventing and/or reducing the risk or likelihood of systemic inflammatory response syndrome (SIRS) and/or sepsis (SIRS/sepsis) and/or diseases related or associated therewith, to pharmaceutical compositions and combinations comprising such active components, and to certain therapeutic uses thereof.

Further, the present invention relates a certain DPP-4 inhibitor (preferably linagliptin, optionally in combination with one or more other active agents) for use in treating, preventing and/or and/or reducing the risk of SIRS/sepsis, which is one or more selected from septic or non-septic SIRS, severe SIRS/sepsis, SIRS/septic shock and multi-organ failure associated with SIRS/sepsis.

Further, the present invention relates a certain DPP-4 inhibitor (preferably linagliptin, optionally in combination with one or more other active agents) for use in treating and/or preventing metabolic diseases, particularly diabetes, especially type 2 diabetes mellitus, and/or conditions related thereto (e.g. diabetic complications), in a patient (particularly human patient) with or at risk of systemic inflammatory response syndrome (SIRS) and/or sepsis (SIRS/sepsis).

Further, the present invention relates to a method of treating, preventing and/or reducing the likelihood or risk of systemic inflammatory response syndrome (SIRS) and/or sepsis (SIRS/sepsis) in a patient (particularly human patient) in need thereof, comprising administering an effective amount of a certain DPP-4 inhibitor (preferably linagliptin), optionally in combination with one or more other active agents, to the patient.

DETAILED DESCRIPTION OF THE INVENTION

Figure 1:
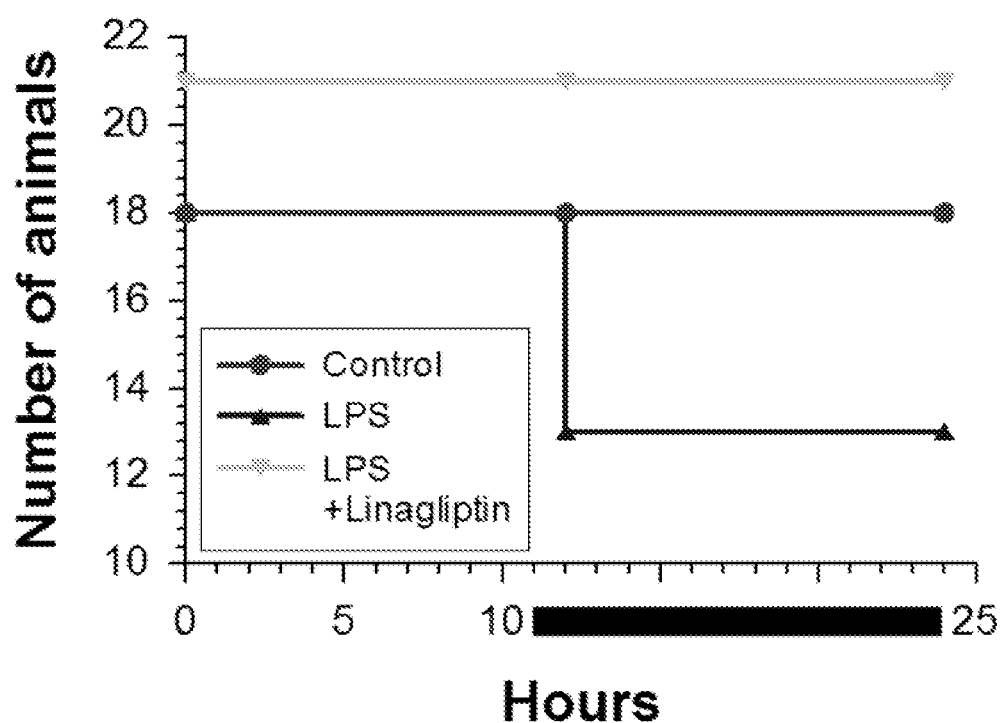
FIG. 1 shows the survival of septic rats with and without linagliptin treatment

Within the scope of the present invention it has now been found that a certain DPP-4 inhibitor (preferably linagliptin) as defined herein as well as pharmaceutical combinations, compositions, uses or methods according to this invention of that DPP-4 inhibitor (preferably linagliptin) optionally in combination with one or more other active agents (such as e.g. a GLP-1 receptor agonist) as defined herein have properties, which make them suitable for the purpose of this invention and/or for fulfilling one or more of the needs mentioned herein.

DPP-4 is analogous to CD26 a T-cell antigene which plays a role in T-cell activation and immuno-modulation. Furthermore, linagliptin, a selective DPP-4 inhibitor further qualifies for the instant purposes with certain anti-oxidative and/or anti-inflammatory features.

Thus, the present invention provides a certain DPP-4 inhibitor as defined herein (preferably linagliptin, optionally in combination with one or more other active agents) for use in treating, preventing and/or reducing the risk of systemic inflammatory response syndrome (SIRS) and/or sepsis (SIRS/sepsis), and/or diseases related or associated therewith.

Further, the present invention relates to a certain DPP-4 inhibitor (preferably linagliptin, optionally in combination with one or more other active agents) for use in increasing survival rate and/or reducing mortality, morbidity or hospitalisation of patients with or at risk of SIRS and/or sepsis (SIRS/sepsis).

Further, the present invention relates to a certain DPP-4 inhibitor (preferably linagliptin, optionally in combination with one or more other active agents) for use in treating, preventing or reducing the likelihood or risk of complications associated with SIRS and/or sepsis, such as e.g. severe SIRS/sepsis, SIRS/septic shock and/or multi-organ failure.

Further, the present invention relates to a certain DPP-4 inhibitor (preferably linagliptin, optionally in combination with one or more other active agents) for use in reducing the risk or likelihood of multi-organ failure in a patient with or at risk of SIRS and/or sepsis (SIRS/sepsis).

Further, the present invention relates to a certain DPP-4 inhibitor (preferably linagliptin, optionally in combination with one or more other active agents) for use in reducing the risk or likelihood of septic shock in a patient with or at risk of SIRS and/or sepsis (SIRS/sepsis).

Further, the present invention relates to a certain DPP-4 inhibitor (preferably linagliptin, optionally in combination with one or more other active agents) for use in reducing the risk or likelihood of severe sepsis in a patient with or at risk of SIRS and/or sepsis (SIRS/sepsis).

Further, the present invention relates to a certain DPP-4 inhibitor (preferably linagliptin, optionally in combination with one or more other active agents) for use in preserving organ function, alleviating multi-organ failure and/or improving survival rate in a patient with or at risk of SIRS and/or sepsis (particularly severe sepsis or septic shock).

Further, the present invention relates to a certain DPP-4 inhibitor (preferably linagliptin, optionally in combination with one or more other active agents) for use in treating, preventing or reducing the likelihood or risk of organ dysfunction, hypoperfusion, perfusion abnormalities and/or hypotension as a complication associated with SIRS/sepsis.

Hypoperfusion or perfusion abnormalities may include, but are not limited to, lactic acidosis, oliguria, or an acute alteration in mental status (e.g. polyneuropathy).

Further, the present invention relates to a certain DPP-4 inhibitor (preferably linagliptin, optionally in combination with one or more other active agents) for use in treating, preventing or reducing the likelihood or risk of dysfunction of cardio- and/or cerebrovascular system, lung, kidney, liver, brain, heart, coagulation system and/or gastrointestinal tract as a complication associated with SIRS/sepsis.

Further, the present invention relates to a certain DPP-4 inhibitor (preferably linagliptin, optionally in combination with one or more other active agents) for use in preventing or reducing the likelihood of a patient suffering from bacteraemia, septicaemia, severe sepsis, septic shock and/or multi-organ failure.

Further, the present invention relates to a certain DPP-4 inhibitor (preferably linagliptin, optionally in combination with one or more other active agents) for use in treating or preventing hypermetabolism, improving metabolic status, normalizing blood glucose levels (glucose homeostasis), decreasing levels of inflammation in blood and/or immunomodulating inflammatory cytokine concentration in blood serum (e.g. in early course of or in newly diagnosed SIRS/sepsis) and/or in preventing or treating organ dysfunction, in a patient with or at risk of SIRS/sepsis.

Further, the present invention relates to a certain DPP-4 inhibitor (preferably linagliptin, optionally in combination with one or more other active agents) for use in treating, preventing or reducing the likelihood or risk of cardiovascular, respiratory, neurologic, hematologic, renal and/or hepatic dysfunction as a complication associated with (severe) SIRS/sepsis.

Further, the present invention relates to a certain DPP-4 inhibitor (preferably linagliptin, optionally in combination with one or more other active agents) for use in preventing or reducing the likelihood that a patient with SIRS acquires an infectious disease and/or sepsis, optionally with complications (e.g. leading to hospitalisation and/or mortal outcome).

Further, the present invention relates to a certain DPP-4 inhibitor (preferably linagliptin, optionally in combination with one or more other active agents) for use in reducing mortality, morbidity, duration or frequency of hospitalization, duration or frequency of bacteraemia, septicaemia, severe sepsis, septic shock, need for dialysis, and/or need for ventilatory support in a patient with or at risk of SIRS/sepsis.

Further, the present invention relates to a certain DPP-4 inhibitor (preferably linagliptin, optionally in combination with one or more other active agents) for use in reducing the likelihood of renal replacement therapy and/or renal failure, in reducing the likelihood of disturbed kidney function parameters, in reducing the likelihood of hyperbilirubinemia, to reducing the likelihood of blood stream infections, in reducing the likelihood of disturbance in markers of inflammations and/or inflammatory responses, in reducing the use of antibiotics, in reducing the amount of red cell transfusion, and/or in reducing stress induced hyperglycaemia, in a patient with or at risk of SIRS/sepsis.

The present invention further provides a certain DPP-4 inhibitor as defined herein (preferably linagliptin, optionally in combination with one or more other active agents) for use in for treating and/or preventing metabolic diseases, particularly diabetes, especially type 2 diabetes mellitus, and/or conditions related thereto (e.g. diabetic complications), in a patient (particularly human patient) with or at risk of systemic inflammatory response syndrome (SIRS) and/or sepsis (SIRS/sepsis).

Examples of metabolic disorders or diseases amenable by the therapy of this invention may include, without being limited to, type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyper-NEFA-emia, postprandial lipemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome.

The present invention further relates to a certain DPP-4 inhibitor (preferably linagliptin, optionally in combination with one or more other active agents) for use in at least one of the following methods:

preventing, slowing the progression of, delaying the onset of or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;

improving and/or maintaining glycemic control and/or for reducing of fasting plasma glucose, of postprandial plasma glucose, of postabsorptive plasma glucose and/or of glycosylated hemoglobin HbA1c, or preventing, reducing the risk of, slowing the progression of, delaying the onset of or treating worsening or deterioration of glycemic control, need for insulin therapy or elevated HbA1c despite treatment;

preventing, slowing, delaying the onset of or reversing progression from pre-diabetes, impaired glucose tolerance (IGT), impaired fasting blood glucose (IFG), insulin resistance and/or from metabolic syndrome to type 2 diabetes mellitus;

preventing, reducing the risk of, slowing the progression of, delaying the onset of or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;

reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat;

preventing, slowing, delaying the onset of or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion;

preventing, slowing, delaying the onset of or treating non alcoholic fatty liver disease (NAFLD) including hepatic steatosis, non-alcoholic steatohepatitis (NASH) and/or liver fibrosis (such as e.g. preventing, slowing the progression, delaying the onset of, attenuating, treating or reversing hepatic steatosis, (hepatic) inflammation and/or an abnormal accumulation of liver fat);

preventing, slowing the progression of, delaying the onset of or treating type 2 diabetes with failure to conventional antidiabetic mono- or combination therapy;

achieving a reduction in the dose of conventional antidiabetic medication required for adequate therapeutic effect;

reducing the risk for adverse effects associated with conventional antidiabetic medication (e.g. hypoglycemia or weight gain); and/or maintaining and/or improving the insulin sensitivity and/or for treating or preventing hyperinsulinemia and/or insulin resistance;

in a patient in need thereof (such as e.g. a patient as described herein, for example a human patient having diabetes), and/or particularly in a patient (particularly human patient) with or at risk of systemic inflammatory response syndrome (SIRS) and/or sepsis (SIRS/sepsis).

In an embodiment, the patient with or at risk of SIRS/sepsis as described herein is diabetic.

In another embodiment, the patient with or at risk of SIRS/sepsis as described herein is non-diabetic.

In a further embodiment, the patient described herein is a subject having diabetes (e.g. type 1 or type 2 diabetes or LADA, particularly type 2 diabetes).

In particular, the subject within this invention may be a human, e.g. human child, a human adolscent or, particularly, a human adult.

Accordingly, in a particular embodiment, a preferred DPP-4 inhibitor within the meaning of this invention is linagliptin.

Pharmaceutical compositions or combinations for use in these therapies (treatments or preventions) comprising a certain DPP-4 inhibitor (preferably linagliptin) as defined herein optionally together with one or more other active agents are also contemplated.

Further, the present invention relates to a certain DPP-4 inhibitor (preferably linagliptin), optionally in combination with one, two or more further active agents, each as defined herein, for use in the therapies (treatments or preventions) as described herein.

Further, the present invention relates to the use of a certain DPP-4 inhibitor (preferably linagliptin), optionally in combination with one, two or more further active agents, each as defined herein, for preparing a pharmaceutical composition which is suitable for the treatment and/or prevention purposes of this invention.

Further, the present invention relates to a therapeutic (treatment or prevention) method as described herein, said method comprising administering an effective amount of a certain DPP-4 inhibitor (preferably linagliptin) and, optionally, one or more other active or therapeutic agents to the patient in need thereof, each as described herein.

Other aspects of the present invention become apparent to the skilled person from the foregoing and following remarks (including the examples and claims).

The aspects of the present invention, in particular the pharmaceutical compounds, compositions, combinations, methods and uses, refer to a certain DPP-4 inhibitor (preferably linagliptin), optionally in combination with one or more other active agents, such as e.g. a GLP-1 receptor agonist, as defined hereinbefore and hereinafter.

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to chronic hyperglycaemia and its associated micro- and macrovascular complications or chronic damages, such as e.g. diabetic nephropathy, retinopathy or neuropathy, or macrovascular (e.g. cardio- or cerebro-vascular) complications. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialised World because of diabetes induced complications and is associated with a two to five fold increase in cardiovascular disease risk.

Furthermore, diabetes (particularly type 2 diabetes) is often coexistent and interrelated with obesity and these two conditions together impose a particularly complex therapeutic challenge. Because of the effects of obesity on insulin resistance, weight loss and its maintainance is an important therapeutic objective in overweight or obese individuals with prediabetes, metabolic syndrome or diabetes. Studies have been demonstrated that weight reduction in subjects with type 2 diabetes is associated with descreased insulin resistance, improved measures of glycemia and lipemia, and reduced blood pressure. Maintainance of weight reduction over longer term is considered to improve glycemic control and prevent diabetic complications (e.g. reduction of risk for cardiovascular diseases or events). Thus, weight loss is recommended for all overweight or obese indivuduals who have or are at risk for diabetes. However, obese patients with type 2 diabetes have much greater difficulty losing weight and maintain the reduced weight than the general non-diabetic population.

Overweight may be defined as the condition wherein the individual has a body mass index (BMI) greater than or 25 $kg/m^2$ and less than 30 $kg/m^2$. The terms "overweight" and "pre-obese" are used interchangeably.

Obesity may be also defined as the condition wherein the individual has a BMI equal to or greater than 30 $kg/m^2$. According to a WHO definition the term obesity may be categorized as follows: class I obesity is the condition wherein the BMI is equal to or greater than 30 $kg/m^2$ but lower than 35 $kg/m^2$; class II obesity is the condition wherein the BMI is equal to or greater than 35 $kg/m^2$ but lower than 40 $kg/m^2$; class III obesity (extreme obesity) is the condition wherein the BMI is equal to or greater than 40 $kg/m^2$. Obesity may include e.g. visceral or abdominal obesity.

Visceral obesity may be defined as the condition wherein a waist-to-hip ratio of greater than or equal to 1.0 in men and 0.8 in women is measured. It defines the risk for insulin resistance and the development of pre-diabetes.

Abdominal obesity may usually be defined as the condition wherein the waist circumference is >40 inches or 102 cm in men, and is >35 inches or 94 cm in women. With regard to a Japanese ethnicity or Japanese patients abdominal obesity may be defined as waist circumference≥85 cm in men and ≥90 cm in women (see e.g. investigating committee for the diagnosis of metabolic syndrome in Japan).

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required. But, because type 2 diabetes is a progressive disease, even patients with good initial responses to conventional combination therapy will eventually require an increase of the dosage or further treatment with insulin because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioriation in metabolic control despite treatment and do not sufficiently control metabolic status especially over long-term and thus fail to achieve and to maintain glycemic control in advanced, progressed or late stage type 2 diabetes, including diabetes with inadequate glycemic control despite conventional oral and/or non-oral antidiabetic medication.

Therefore, although intensive treatment of hyperglycemia can reduce the incidence of chronic damages, many patients with diabetes remain inadequately treated, partly because of limitations in long term efficacy, tolerability and dosing inconvenience of conventional antihyperglycemic therapies.

In addition, obesity, overweight or weight gain (e.g. as side or adverse effect of some conventional antidiabetic medications) further complicates the treatment of diabetes and its microvascular or macrovascular complications.

This high incidence of therapeutic failure is a major contributor to the high rate of long-term hyperglycemia-associated complications or chronic damages (including micro- and makrovascular complications such as e.g. diabetic nephrophathy, retinopathy or neuropathy, or cerebro- or cardiovascular complications such as e.g. myocardial infarction, stroke or vascular mortality or morbidity) in patients with diabetes.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, glinides and α-glucosidase inhibitors.

Non-oral (typically injected) antidiabetic drugs conventionally used in therapy (such as e.g. first- or second-line, and/or mono- or (initial or add-on) combination therapy) include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting).

Therefore, it remains a need in the art to provide efficacious, safe and tolerable antidiabetic therapies.

Further, within the therapy of type 2 diabetes, it is a need for treating the condition effectively, avoiding the complications inherent to the condition, and delaying disease progression, e.g. in order to achieve a long-lasting therapeutic benefit.

Furthermore, it remains a need that antidiabetic treatments not only prevent the long-term complications often found in advanced stages of diabetes disease, but also are a therapeutic option in those diabetes patients who have developed or are at risk of developing complications, such as renal impairment.

Moreover, it remains a need to provide prevention or reduction of risk for adverse effects associated with conventional antidiabetic therapies.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945.

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <7.0%, preferably <6.5% and more preferably <6% HbA1c.

Within the meaning of this invention, inadequate or insufficient glycemic control means in particular a condition wherein patients show HbA1c values above 6.5%, in particular above 7.0%, even more preferably above 7.5%, especially above 8%. An embodiment of patients with inadequate or insufficient glycemic control include, without being limited to, patients having a HbA1c value from 7.5 to 10% (or, in another embodiment, from 7.5 to 11%). A special sub-embodiment of inadequately controlled patients refers to patients with poor glycemic control including, without being limited, patients having a HbA1c value 9%.

Within glycemic control, in addition to improvement of the HbA1c level, other recommended therapeutic goals for type 2 diabetes mellitus patients are improvement of fasting plasma glucose (FPG) and of postprandial plasma glucose (PPG) levels to normal or as near normal as possible. Recommended desired target ranges of preprandial (fasting) plasma glucose are 70-130 mg/dL (or 90-130 mg/dL) or <110 mg/dL, and of two-hour postprandial plasma glucose are <180 mg/dL or <140 mg/dL.

In one embodiment, diabetes patients within the meaning of this invention may include patients who have not previously been treated with an antidiabetic drug (drug-naïve patients). Thus, in an embodiment, the therapies described herein may be used in naïve patients. In another embodiment, diabetes patients within the meaning of this invention may include patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein.

A further embodiment of diabetic patients within the meaning of this invention refers to patients ineligible for metformin therapy including patients for whom metformin therapy is contraindicated, e.g. patients having one or more contraindications against metformin therapy according to label, such as for example patients with at least one contraindication selected from:
renal disease, renal impairment or renal dysfunction (e.g., as specified by product information of locally approved metformin),
dehydration,
unstable or acute congestive heart failure,
acute or chronic metabolic acidosis, and
hereditary galactose intolerance;
and
patients who suffer from one or more intolerable side effects attributed to metformin, particularly gastrointestinal side effects associated with metformin, such as for example patients suffering from at least one gastrointestinal side effect selected from:
nausea,
vomiting,
diarrhoea,
intestinal gas, and
severe abdominal discomfort.

A further embodiment of the diabetes patients which may be amenable to the therapies of this invention may include, without being limited, those diabetes patients for whom normal metformin therapy is not appropriate, such as e.g. those diabetes patients who need reduced dose metformin therapy due to reduced tolerability, intolerability or contraindication against metformin or due to (mildly) impaired/reduced renal function (including elderly patients, such as e.g. ≥60-65 years).

A further embodiment of patients (e.g. which may be diabetic or non-diabetic) within the meaning of this invention refers to patients having renal disease, renal dysfunction, or insufficiency or impairment of renal function (including mild, moderate and severe renal impairment), e.g. as suggested by elevated serum creatinine levels (e.g. serum creatinine levels above the upper limit of normal for their age, e.g. ≥130-150 μmol/l, or ≥1.5 mg/dl (≥136 μmol/l) in men and ≥1.4 mg/dl (≥124 μmol/l) in women) or abnormal creatinine clearance (e.g. glomerular filtration rate (GFR) ≤30-60 ml/min).

In this context, for more detailed example, mild renal impairment may be e.g. suggested by a creatinine clearance of 50-80 ml/min (approximately corresponding to serum creatine levels of ≤1.7 mg/dL in men and 1.5 mg/dL in women); moderate renal impairment may be e.g. suggested by a creatinine clearance of 30-50 ml/min (approximately corresponding to serum creatinine levels of >1.7 to ≤3.0 mg/dL in men and >1.5 to ≤2.5 mg/dL in women); and severe renal impairment may be e.g. suggested by a creatinine clearance of <30 ml/min (approximately corresponding to serum creatinine levels of >3.0 mg/dL in men and >2.5 mg/dL in women). Patients with end-stage renal disease require dialysis (e.g. hemodialysis or peritoneal dialysis).

For other more detailed example, patients with renal disease, renal dysfunction or renal impairment include patients with chronic renal insufficiency or impairment, which can be stratified according to glomerular filtration rate (GFR, ml/min/1.73 m$^2$) into 5 disease stages: stage 1 characterized by normal GFR≥90 plus either persistent albuminuria or known structural or hereditary renal disease; stage 2 characterized by mild reduction of GFR (GFR 60-89) describing mild renal impairment; stage 3 characterized by moderate reduction of GFR (GFR 30-59) describing moderate renal impairment; stage 4 characterized by severe reduction of GFR (GFR 15-29) describing severe renal impairment; and terminal stage 5 characterized by requiring dialysis or GFR<15 describing established kidney failure (end-stage renal disease, ESRD).

A further embodiment of patients (e.g. which may be diabetic or non-diabetic) within the meaning of this invention refers to diabetes patients with or at risk of developing renal complications, such as diabetic nephropathy (including chronic and progressive renal insufficiency, albuminuria, proteinuria, fluid retention in the body (edema) and/or hypertension).

In certain embodiments, the patients which may be amenable to the therapies of this invention may have or are at-risk of one or more of the following diseases, disorders or conditions: type 1 diabetes, type 2 diabetes, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia (including e.g. atherogenic dyslipidemia), hyperlipidemia, hypercholesterolemia, hypertriglyceridemia, hyperNEFA-emia, postprandial lipemia, hypertension, atherosclerosis, endothelial dysfunction, osteoporosis, chronic systemic inflammation, non alcoholic fatty liver disease (NAFLD), polycystic ovarian syndrome, hyperuricemia, metabolic syndrome, nephropathy, micro- or macroalbuminuria, proteinuria, retinopathy, cataracts, neuropathy, learning or memory impairment, neurodegenerative or cognitive disorders, cardio- or cerebro-vascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries, (renal, cardiac, cerebral or hepatic) fibrosis, (renal, cardiac, cerebral or hepatic) vascular remodelling; a diabetic disease, e.g. type 2 diabetes mellitus being (with or without obesity) being particularly to be noted (e.g. as an underlying disease).

In a further embodiment, the patients with or at-risk of SIRS/sepsis which may be amenable to the therapies of this invention have a diabetic disease, such as e.g. type 2 diabetes mellitus, and, optionally, may have or are at-risk of one or more other diseases, disorders or conditions, such as e.g. selected from those mentioned immediately above.

Accordingly, the present invention thus relates to a certain DPP-4 inhibitor as defined herein, preferably linagliptin (BI 1356), for use in the therapies (treatments and/or preventions) described herein.

The present invention further relates to a certain DPP-4 inhibitor as defined herein, preferably linagliptin (BI 1356), in combination with metformin, for use in the therapies (treatments and/or preventions) described herein.

The present invention further relates to a certain DPP-4 inhibitor as defined herein, preferably linagliptin (BI 1356), in combination with pioglitazone, for use in the therapies (treatments and/or preventions) described herein.

The present invention further relates to a certain DPP-4 inhibitor as defined herein, preferably linagliptin (BI 1356), in combination with telmisartan, for use in the therapies (treatments and/or preventions) described herein.

The present invention further relates to a certain DPP-4 inhibitor as defined herein, preferably linagliptin (BI 1356), in combination with a GLP-1 receptor agonist (such as e.g. exenatide, exenatide LAR, liraglutide, taspoglutide, semaglutide, albiglutide, lixisenatide, dulaglutide, or native GLP-1) for use in the therapies (treatments and/or preventions) described herein.

The present invention further relates to a certain DPP-4 inhibitor as defined herein, preferably linagliptin (BI 1356), in combination with one or more other active agents, e.g. selected from other antidiabetic substances, active substances that lower the blood sugar level, active substances that lower the lipid level in the blood, active substances that raise the HDL level in the blood, active substances that lower blood pressure, and active substances that are indicated in the treatment of atherosclerosis or obesity, for use in the therapies (treatments and/or preventions) described herein.

The present invention further relates to a certain DPP-4 inhibitor as defined herein, preferably linagliptin (BI 1356), in combination with one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, optionally in combination with one or more further active agents (e.g. telmisartan), for use in the therapies (treatments and/or preventions) described herein.

The present invention further relates to a pharmaceutical composition comprising a certain DPP-4 inhibitor as defined herein, preferably linagliptin (BI 1356), for use in the therapies described herein.

The present invention further relates to a pharmaceutical composition comprising a certain DPP-4 inhibitor as defined herein, preferably linagliptin (BI 1356), and metformin, for use in the therapies described herein.

The present invention further relates to a pharmaceutical composition comprising a certain DPP-4 inhibitor as defined herein, preferably linagliptin (BI 1356), and pioglitazone, for use in the therapies described herein.

The present invention further relates to a combination comprising a certain DPP-4 inhibitor (particularly linagliptin) and one or more other active agents selected from those mentioned herein, e.g. selected from other antidiabetic substances, active substances that lower the blood sugar level, active substances that lower the lipid level in the blood, active substances that raise the HDL level in the blood, active substances that lower blood pressure, active substances that are indicated in the treatment of atherosclerosis or obesity, e.g. each as described herein; particularly for simultaneous, separate or sequential use in the therapies described herein.

The present invention further relates to a combination comprising a certain DPP-4 inhibitor (particularly linagliptin) and one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, particularly for simultaneous, separate or sequential use in the therapies described herein, optionally in combination with telmisartan.

The present invention further relates to therapies or therapeutic or preventive methods or uses as described herein, such as e.g. to a method for treating and/or preventing a metabolic disease, such as e.g. type 2 diabetes mellitus and/or conditions related thereto (e.g. diabetic complications) comprising administering (e.g. simultaneously, separately or sequentially) an effective amount of a certain DPP-4 inhibitor (particularly linagliptin) as defined herein and, optionally, one or more other active agents, such as e.g. one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, optionally in combination with one or more further active agents (e.g. telmisartan), to the patient (particularly human patient) in need thereof, such as e.g. a patient as described herein, including a patient with or at risk of SIRS and/or sepsis.

The present invention further relates to therapies or therapeutic or preventive methods or uses as described herein, such as e.g. a method for treating and/or preventing a metabolic disease, such as e.g. type 2 diabetes mellitus and/or conditions related thereto (e.g. diabetic complications), comprising administering an effective amount of linagliptin (BI 1356) and metformin, and optionally one or more further active agents, to the patient (particularly human patient) in need thereof, such as e.g. a patient as described herein, including a patient with or at risk of SIRS and/or sepsis.

The present invention further relates to therapies or therapeutic or preventive methods or uses as described herein, such as e.g. a method for treating and/or preventing a metabolic disease, such as e.g. type 2 diabetes mellitus and/or conditions related thereto (e.g. diabetic complications), comprising administering an effective amount of linagliptin (BI 1356) and pioglitazone, and optionally one or more further active agents, to the patient (particularly human patient) in need thereof, such as e.g. a patient as described herein, including a patient with or at risk of SIRS and/or sepsis.

The present invention further relates to therapies or therapeutic or preventive methods or uses as described herein, such as e.g. a method for treating and/or preventing a metabolic disease, such as e.g. type 2 diabetes mellitus and/or conditions related thereto (e.g. diabetic complications), comprising administering an effective amount of linagliptin (BI 1356) and telmisartan, and optionally one or more further active agents, to the patient (particularly human patient) in need thereof, such as e.g. a patient as described herein, including a patient with or at risk of SIRS and/or sepsis.

Further, the present invention relates to a method of treating, preventing and/or reducing the risk of systemic inflammatory response syndrome (SIRS) and/or sepsis (SIRS/sepsis) in a patient (particularly a human patient, who may suffer from diabetes, e.g. type 1 or type 2 diabetes or LADA, particularly type 2 diabetes, or who may be non-diabetic) in need thereof, comprising administering an effective amount of linagliptin, optionally in combination with one or more other active agents (such as e.g. a GLP-1 receptor agonist), to the patient.

Further, the present invention relates to a method of treating, preventing and/or reducing the risk of systemic inflammatory response syndrome (SIRS) and/or sepsis (SIRS/sepsis) in a patient (particularly a human patient, who may suffer from diabetes, e.g. type 1 or type 2 diabetes or LADA, particularly type 2 diabetes, or who may be non-diabetic) in need thereof, comprising administering an effective amount of linagliptin, optionally in combination with one or more other active agents, e.g. selected from other antidiabetic substances, active substances that lower the blood sugar level, active substances that lower the lipid level in the blood, active substances that raise the HDL level in the blood, active substances that lower blood pressure, and active substances that are indicated in the treatment of atherosclerosis or obesity, to the patient.

Further, the present invention relates to a method of treating, preventing and/or reducing the risk of systemic inflammatory response syndrome (SIRS) and/or sepsis (SIRS/sepsis) in a patient (particularly a human patient, who may suffer from diabetes, e.g. type 1 or type 2 diabetes or LADA, particularly type 2 diabetes, or who may be non-diabetic) in need thereof, comprising administering an effective amount of linagliptin and one or more other antidiabetics selected from the group consisting of metformin, a sulphonylurea, nateglinide, repaglinide, a thiazolidinedione, a PPAR-gamma-agonist, an alpha-glucosidase inhibitor, insulin or an insulin analogue, and GLP-1 or a GLP-1 analogue, optionally in combination with one or more further active agents (e.g. telmisartan), to the patient.

A DPP-4 inhibitor within the meaning of the present invention includes, without being limited to, any of those DPP-4 inhibitors mentioned hereinabove and hereinbelow, preferably orally and/or subcutaneously active DPP-4 inhibitors.

In a first embodiment (embodiment A), a DPP-4 inhibitor in the context of the present invention is any DPP-4 inhibitor of formula (I)

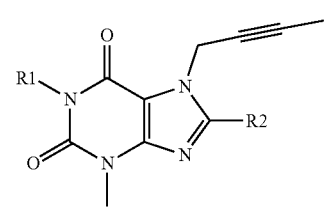

or formula (II)

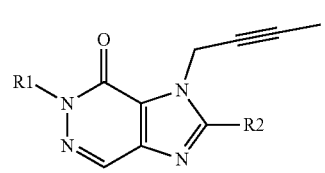

or formula (III)

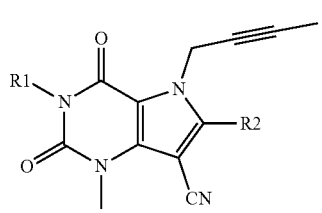

or formula (IV)

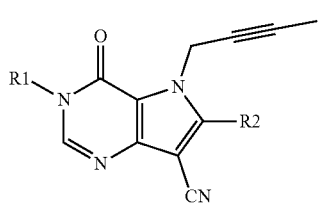

wherein R1 denotes ([1,5]naphthyridin-2-yl)methyl, (quinazolin-2-yl)methyl, (quinoxalin-6-yl)methyl, (4-methyl-quinazolin-2-yl)methyl, 2-cyano-benzyl, (3-cyano-quinolin-2-yl)methyl, (3-cyano-pyridin-2-yl) methyl, (4-methyl-pyrimidin-2-yl)methyl, or (4,6-dimethyl-pyrimidin-2-yl)methyl and R2 denotes 3-(R)-amino-piperidin-1-yl, (2-amino-2-methyl-propyl)-methylamino or (2-(S)-amino-propyl)-methylamino, or its pharmaceutically acceptable salt.

Regarding the first embodiment (embodiment A), preferred DPP-4 inhibitors are any or all of the following compounds and their pharmaceutically acceptable salts:

1-[(4-methyl-quinazolin-2-yl)methyl]-3-methyl-7-(2-butyn-1-yl)-8-(3-(R)-amino-piperidin-1-yl)-xanthine (compare WO 2004/018468, example 2(142))

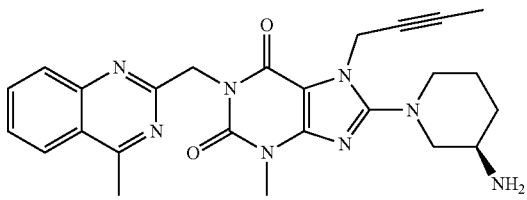 [SMILES: CC#CCn1c(N2CCC[C@@H](N)C2)nc2c1c(=O)n(Cc1nc(C)c3ccccc3n1)c(=O)n2C]

1-[([1,5]naphthyridin-2-yl)methyl]-3-methyl-7-(2-butyn-1-yl)-8-((R)-3-amino-piperidin-1-yl)-xanthine (compare WO 2004/018468, example 2(252))

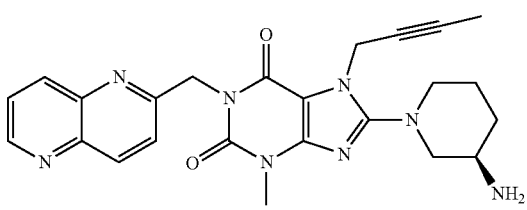 [SMILES: CC#CCn1c(N2CCC[C@@H](N)C2)nc2c1c(=O)n(Cc1ccc3ncccc3n1)c(=O)n2C]

1-[(Quinazolin-2-yl)methyl]-3-methyl-7-(2-butyn-1-yl)-8-((R)-3-amino-piperidin-1-yl)-xanthine (compare WO 2004/018468, example 2(80))

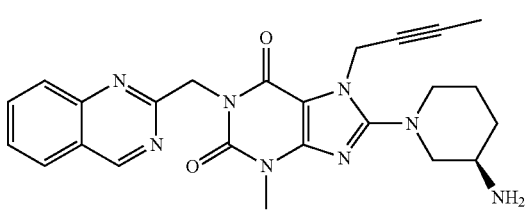 [SMILES: CC#CCn1c(N2CCC[C@@H](N)C2)nc2c1c(=O)n(Cc1ncc3ccccc3n1)c(=O)n2C]

2-((R)-3-Amino-piperidin-1-yl)-3-(but-2-yinyl)-5-(4-methyl-quinazolin-2-ylmethyl)-3,5-dihydro-imidazo[4,5-d]pyridazin-4-one (compare WO 2004/050658, example 136)

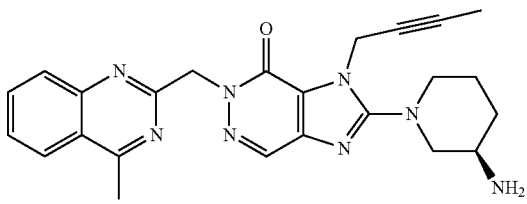 [SMILES: CC#CCn1c(N2CCC[C@@H](N)C2)nc2cnn(Cc3nc(C)c4ccccc4n3)c(=O)c21]

1-[(4-Methyl-quinazolin-2-yl)methyl]-3-methyl-7-(2-butyin-1-yl)-8-[(2-amino-2-methyl-propyl)-methylamino]-xanthine (compare WO 2006/029769, example 2(1))

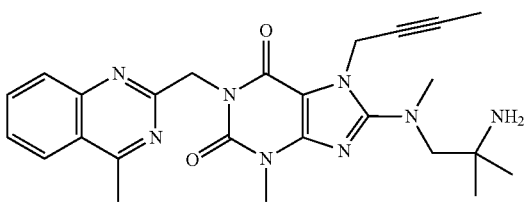 [SMILES: CC#CCn1c(N(C)CC(C)(C)N)nc2c1c(=O)n(Cc1nc(C)c3ccccc3n1)c(=O)n2C]

1-[(3-Cyano-quinolin-2-yl)methyl]-3-methyl-7-(2-butyn-1-yl)-8-((R)-3-amino-piperidin-1-yl)-xanthine (compare WO 2005/085246, example 1(30))

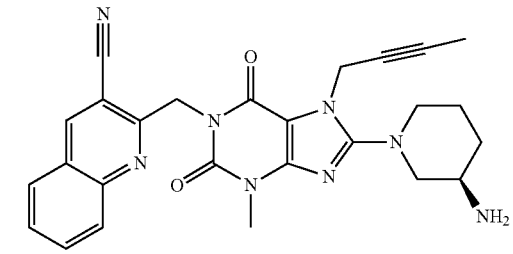 [SMILES: CC#CCn1c(N2CCC[C@@H](N)C2)nc2c1c(=O)n(Cc1nc3ccccc3cc1C#N)c(=O)n2C]

1-(2-Cyano-benzyl)-3-methyl-7-(2-butyn-1-yl)-8-((R)-3-amino-piperidin-1-yl)-xanthine (compare WO 2005/085246, example 1(39))

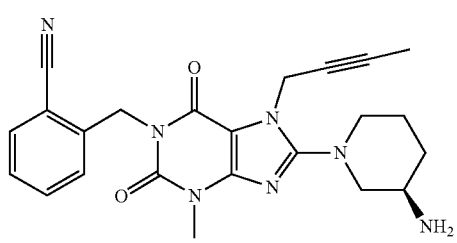 [SMILES: CC#CCn1c(N2CCC[C@@H](N)C2)nc2c1c(=O)n(Cc1ccccc1C#N)c(=O)n2C]

1-[(4-Methyl-quinazolin-2-yl)methyl]-3-methyl-7-(2-butyn-1-yl)-8-[(S)-(2-amino-propyl)-methylamino]-xanthine (compare WO 2006/029769, example 2(4))

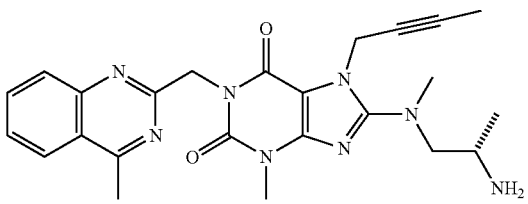 [SMILES: CC#CCn1c(N(C)C[C@H](C)N)nc2c1c(=O)n(Cc1nc(C)c3ccccc3n1)c(=O)n2C]

1-[(3-Cyano-pyridin-2-yl)methyl]-3-methyl-7-(2-butyn-1-yl)-8-((R)-3-amino-piperidin-1-yl)-xanthine (compare WO 2005/085246, example 1(52))

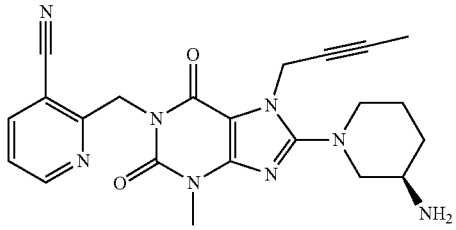 [SMILES: CC#CCn1c(N2CCC[C@@H](N)C2)nc2c1c(=O)n(Cc1ncccc1C#N)c(=O)n2C]

1-[(4-Methyl-pyrimidin-2-yl)methyl]-3-methyl-7-(2-butyn-1-yl)-8-((R)-3-amino-piperidin-1-yl)-xanthine (compare WO 2005/085246, example 1(81))

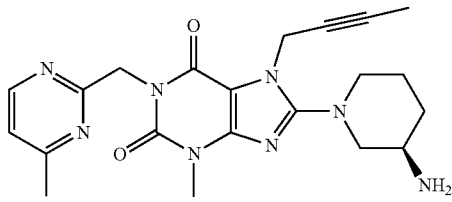 [SMILES: CC#CCn1c(N2CCC[C@@H](N)C2)nc2c1c(=O)n(Cc1nccc(C)n1)c(=O)n2C]

1-[(4,6-Dimethyl-pyrimidin-2-yl)methyl]-3-methyl-7-(2-butyn-1-yl)-8-((R)-3-amino-piperidin-1-yl)-xanthine (compare WO 2005/085246, example 1(82))

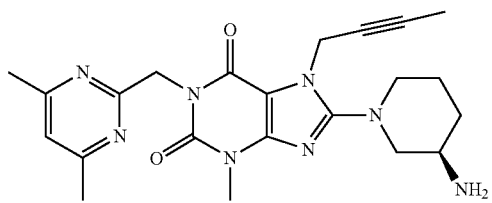 [SMILES: CC#CCn1c(N2CCC[C@@H](N)C2)nc2c1c(=O)n(Cc1nc(C)cc(C)n1)c(=O)n2C]

1-[(Quinoxalin-6-yl)methyl]-3-methyl-7-(2-butyn-1-yl)-8-((R)-3-amino-piperidin-1-yl)-xanthine (compare WO 2005/085246, example 1(83))

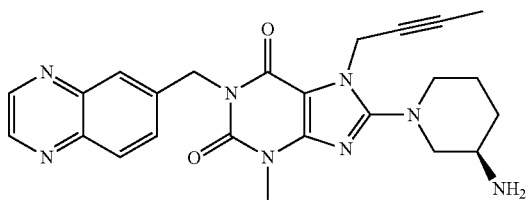 [SMILES: CC#CCn1c(N2CCC[C@@H](N)C2)nc2c1c(=O)n(Cc1ccc3nccnc3c1)c(=O)n2C]

These DPP-4 inhibitors are distinguished from structurally comparable DPP-4 inhibitors, as they combine exceptional potency and a long-lasting effect with favourable pharmacological properties, receptor selectivity and a favourable side-effect profile or bring about unexpected therapeutic advantages or improvements when combined with other pharmaceutical active substances. Their preparation is disclosed in the publications mentioned.

In a second embodiment (embodiment B), a DPP-4 inhibitor in the context of the present invention is a DPP-4 inhibitor selected from the group consisting of sitagliptin, vildagliptin, saxagliptin, alogliptin, gemigliptin, (2S)-1-{[2-(5-Methyl-2-phenyl-oxazol-4-yl)-ethylamino]-acetyl}-pyrrolidine-2-carbonitrile, (2S)-1-{[1,1,-Dimethyl-3-(4-pyridin-3-yl-imidazol-1-yl)-propylamino]-acetyl}-pyrrolidine-2-carbonitrile, (S)-1-((2S,3S,11bS)-2-Amino-9,10-dimethoxy-1,3,4,6,7,11b-hexahydro-2H-pyrido[2,1-a]isoquinolin-3-yl)-4-fluoromethyl-pyrrolidin-2-one, (3,3-Difluoropyrrolidin-1-yl)-((2S,4S)-4-(4-(pyrimidin-2-yl)piperazin-1-yl)pyrrolidin-2-yl)methanone, (1((3S,4S)-4-amino-1-(4-(3,3-difluoropyrrolidin-1-yl)-1,3,5-triazin-2-yl)pyrrolidin-3-yl)-5,5-difluoropiperidin-2-one, (2S,4S)-1-{2-[(3S,1R)-3-(1H-1,2,4-Triazol-1-ylmethyl)cyclopentylamino]-acetyl}-4-fluoropyrrolidine-2-carbonitrile, (R)-2-[6-(3-Amino-piperidin-1-yl)-3-methyl-2,4-dioxo-3,4-dihydro-2H-pyrimidin-1-ylmethyl]-4-fluoro-benzonitrile, 5-{(S)-2-[2-((S)-2-Cyano-pyrrolidin-1-yl)-2-oxo-ethylamino]-propyl}-5-(1H-tetrazol-5-yl)-10,11-dihydro-5H-dibenzo[a,d]cycloheptene-2,8-dicarboxylic acid bis-dimethylamide, 3-{(2S,4S)-4-[4-(3-Methyl-1-phenyl-1H-pyrazol-5-yl)piperazin-1-yl]pyrrolidin-2-ylcarbonyl}thiazolidine,

[(2R)-1-{[(3R)-pyrrolidin-3-ylamino]acetyl}pyrrolidin-2-yl]boronic acid, (2S,4S)-1-[2-[(4-ethoxycarbonylbicyclo[2.2.2]oct-1-yl)amino]acetyl]-4-fluoropyrrolidine-2-carbonitrile, 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile, 6-[(3R)-3-amino-piperidin-1-yl]-5-(2-chloro-5-fluoro-benzyl)-1,3-dimethyl-1,5-dihydro-pyrrolo[3,2-d]pyrimidine-2,4-dione, and (S)-2-methylpyrazolo[1,5-a]primidine-6-carboxylic acid {2-[(2-cyanopyrrolidin-1-yl)-2-oxoethylamino]-2-methylpropyl}amide, or its pharmaceutically acceptable salt.

A more preferred DPP-4 inhibitor among the abovementioned DPP-4 inhibitors of embodiment A of this invention is 1-[(4-methyl-quinazolin-2-yl)methyl]-3-methyl-7-(2-butyn-1-yl)-8-(3-(R)-amino-piperidin-1-yl)-xanthine, particularly the free base thereof (which is also known as linagliptin or BI 1356).

Preferably the DPP-4 inhibitor of this invention is selected from the group consisting of linagliptin, sitagliptin, vildagliptin, alogliptin, saxagliptin, teneligliptin, anagliptin, gemigliptin and dutogliptin, or a pharmaceutically acceptable salt of one of the hereinmentioned DPP-4 inhibitors, or a prodrug thereof.

A particularly preferred DPP-4 inhibitor to be emphasized within the present invention is linagliptin. The term "linagliptin" as employed herein refers to linagliptin or a pharmaceutically acceptable salt thereof, including hydrates and solvates thereof, and crystalline forms thereof, preferably linagliptin refers to 1-[(4-methyl-quinazolin-2-yl)methyl]-3-methyl-7-(2-butyn-1-yl)-8-(3-(R)-amino-piperidin-1-yl)-xanthine. Crystalline forms are described in WO 2007/

128721. Methods for the manufacture of linagliptin are described in the patent applications WO 2004/018468 and WO 2006/048427 for example. Linagliptin is distinguished from structurally comparable DPP-4 inhibitors, as it combines exceptional potency and a long-lasting effect with favourable pharmacological properties, receptor selectivity and a favourable side-effect profile or bring about unexpected therapeutic advantages or improvements in mono- or dual or triple combination therapy.

For avoidance of any doubt, the disclosure of each of the foregoing and following documents cited above in connection with the specified DPP-4 inhibitors is specifically incorporated herein by reference in its entirety.

An embodiment of this invention refers to a DPP-4 inhibitor suitable for use in the treatment and/or prevention of metabolic diseases (particularly type 2 diabetes mellitus) in patients, wherein said patients further suffering from renal disease, renal dysfunction or renal impairment, particularly characterized in that said DPP-4 inhibitor is administered to said patients in the same dose levels as to patients with normal renal function, thus e.g. said DPP-4 inhibitor does not require downward dosing adjustment for impaired renal function.

For example, a DPP-4 inhibitor according to this invention (especially one which may be suited for patients with impaired renal function) may be such an oral DPP-4 inhibitor, which and whose active metabolites have preferably a relatively wide (e.g. about >100 fold) therapeutic window and/or, especially, that are primarily eliminated via hepatic metabolism or biliary excretion (preferably without adding additional burden to the kidney).

In more detailed example, a DPP-4 inhibitor according to this invention (especially one which may be suited for patients with impaired renal function) may be such an orally administered DPP-4 inhibitor, which has a relatively wide (e.g. >100 fold) therapeutic window (preferably a safety profile comparable to placebo) and/or which fulfils one or more of the following pharmacokinetic properties (preferably at its therapeutic oral dose levels):

The DPP-4 inhibitor is substantially or mainly excreted via the liver (e.g. >80% or even >90% of the administered oral dose), and/or for which renal excretion represents no substantial or only a minor elimination pathway (e.g. <10%, preferably <7%, of the administered oral dose measured, for example, by following elimination of a radiolabelled carbon ($^{14}C$) substance oral dose);

The DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}C$) substance), and/or which is eliminated to a non-substantial or only to a minor extent via metabolism (e.g. <30%, or <20%, or, preferably, 10%);

The (main) metabolite(s) of the DPP-4 inhibitor is/are pharmacologically inactive. Such as e.g. the main metabolite does not bind to the target enzyme DPP-4 and, optionally, it is rapidly eliminated compared to the parent compound (e.g. with a terminal half-life of the metabolite of ≤20 h, or, preferably, ≤ about 16 h, such as e.g. 15.9 h).

In one embodiment, the (main) metabolite in plasma (which may be pharmacologically inactive) of a DPP-4 inhibitor having a 3-amino-piperidin-1-yl substituent is such a derivative where the amino group of the 3-amino-piperidin-1-yl moiety is replaced by a hydroxyl group to form the 3-hydroxy-piperidin-1-yl moiety (e.g. the 3-(S)-hydroxy-piperidin-1-yl moiety, which is formed by inversion of the configuration of the chiral center).

Further properties of a DPP-4 inhibitor according to this invention may be one or more of the following: Rapid attainment of steady state (e.g. reaching steady state plasma levels (>90% of the steady state plasma concentration) between second and fifth day of treatment with therapeutic oral dose levels), little accumulation (e.g. with a mean accumulation ratio $R_{A,AUC}$≤1.4 with therapeutic oral dose levels), and/or preserving a long-lasting effect on DPP-4 inhibition, preferably when used once-daily (e.g. with almost complete (>90%) DPP-4 inhibition at therapeutic oral dose levels, >80% inhibition over a 24 h interval after once-daily intake of therapeutic oral drug dose), significant decrease in 2 h postprandial blood glucose excursions by ≥80% (already on first day of therapy) at therapeutic dose levels, and cumulative amount of unchanged parent compound excreted in urine on first day being below 1% of the administered dose and increasing to not more than about 3-6% in steady state.

Thus, for example, a DPP-4 inhibitor according to this invention may be characterized in that said DPP-4 inhibitor has a primarily non-renal route of excretion, i.e. said DPP-4 inhibitor is excreted to a non-substantial or only to a minor extent (e.g. <10%, preferably <7%, e.g. about 5%, of administered oral dose, preferably of oral therapeutic dose) via the kidney (measured, for example, by following elimination of a radiolabelled carbon ($^{14}C$) substance oral dose).

Further, a DPP-4 inhibitor according to this invention may be characterized in that said DPP-4 inhibitor is excreted substantially or mainly via the liver, bile or faeces (measured, for example, by following elimination of a radiolabelled carbon ($^{14}C$) substance oral dose).

Further, a DPP-4 inhibitor according to this invention may be characterized in that said DPP-4 inhibitor is excreted mainly unchanged as parent drug (e.g. with a mean of >70%, or >80%, or, preferably, 90% of excreted radioactivity in urine and faeces after oral dosing of radiolabelled carbon ($^{14}C$) substance), said DPP-4 inhibitor is eliminated to a non-substantial or only to a minor extent via metabolism, and/or the main metabolite of said DPP-4 inhibitor is pharmacologically inactive or has a relatively wide therapeutic window.

Further, a DPP-4 inhibitor according to this invention may be characterized in that said DPP-4 inhibitor does not significantly impair glomerular and/or tubular function of a type 2 diabetes patient with chronic renal insufficiency (e.g. mild, moderate or severe renal impairment or end stage renal disease), and/or said DPP-4 inhibitor trough levels in the blood plasma of type 2 diabetes patients with mild or moderate renal impairment are comparable to the levels in patients with normal renal function, and/or said DPP-4 inhibitor does not require to be dose-adjusted in a type 2 diabetes patient with impaired renal function (e.g. mild, moderate or severe renal impairment or end stage renal disease, preferably regardless of the stage of renal impairment).

Further, a DPP-4 inhibitor according to this invention may be characterized in that said DPP-4 inhibitor provides its minimally effective dose at that dose that results in >50% inhibition of DPP-4 activity at trough (24 h after last dose) in >80% of patients, and/or said DPP-4 inhibitor provides its fully therapeutic dose at that dose that results in >80% inhibition of DPP-4 activity at trough (24 h after last dose) in >80% of patients.

Further, a DPP-4 inhibitor according to this invention may be characterized in that being suitable for use in type 2 diabetes patients who are with diagnosed renal impairment or complication and/or who are at risk of developing renal complications, e.g. patients with or at risk of diabetic nephropathy (including chronic and progressive renal insufficiency, albuminuria, proteinuria, fluid retention in the body (edema) and/or hypertension).

GLP-1 receptor agonists include, without being limited, exogenous GLP-1 (natural or synthetic), GLP-1 mimetics or analogues (including longer acting analogues which are resistant to or have reduced susceptibility to enzymatic degradation by DPP-4 and NEP 24.11) and other substances (whether peptidic or non-peptidic, e.g. small molecules) which promote signalling through the GLP-1 receptor.

Examples of GLP-1 analogues may include (group G2): exenatide (synthetic exendin-4, e.g. formulated as Byetta); exenatide LAR (long acting release formulation of exenatide, e.g. formulated as Bydureon); liraglutide (e.g. formulated as Victoza); taspoglutide; semaglutide; albiglutide (e.g. formulated as Syncria); lixisenatide; dulaglutide; and the di-PEGylated GLP-1 compound comprising the amino acid sequence of the pegylated compound of Formula I (SEQ ID NO:1) according to WO 2006/124529 (the disclosure of which is incorporated herein), wherein $Xaa_8$ is Val, $Xaa_{22}$ is Glu, $Xaa_{33}$ is Ile, and $Xaa_{46}$ is Cys-$NH_2$, and wherein one PEG molecule is covalently attached to $Cys_{45}$ and one PEG molecule is covalently attached to $Cys_{46}$-$NH_2$, wherein each of the PEG molecules used for PEGylation reaction is a 20,000 dalton linear methoxy PEG maleimide, preferably the GLP-1 derivative consists of the amino acid sequence of Val-Glu-Ile-Cys-$NH_2$-GLP-1 (SEQ ID NO: 1). (See also WO 2009/020802, the disclosure of which is incorporated herein).

Preferred examples of GLP-1 receptor agonists (GLP-1 analogues) of this invention are exenatide, exenatide LAR, liraglutide, taspoglutide, semaglutide, albiglutide, lixisenatide and dulaglutide.

GLP-1 analogues have typically significant sequence identity to GLP-1 (e.g. greater than 50%, 75%, 90% or 95%) and may be derivatised, e.g. by conjunction to other proteins (e.g. albumin or IgG-Fc fusion protein) or through chemical modification.

In an embodiment, the GLP-1 receptor agonist is preferably administered by injection (preferably subcutaneously).

Unless otherwise noted, according to this invention it is to be understood that the definitions of the active agents (including the DPP-4 inhibitors and GLP-1 receptor agonists) mentioned hereinabove and hereinbelow may also contemplate their pharmaceutically acceptable salts, and prodrugs, hydrates, solvates and polymorphic forms thereof. Particularly the terms of the therapeutic agents given herein refer to the respective active drugs. With respect to salts, hydrates and polymorphic forms thereof, particular reference is made to those which are referred to herein.

An effective amount of a compound as used herein means an amount sufficient to cure, alleviate or partially arrest the clinical manifestations of a given state or condition, such as a disease or disorder, and its complications. An amount adequate to accomplish this is defined as "effective amount". Effective amounts for each purpose will depend on the severity of the condition, disease or injury as well as the weight and general state of the subject and mode of administration, or the like. It will be understood that determining an appropriate dosage may be achieved using routine experimentation, e.g. by constructing a matrix of values and testing different points in the matrix, which is all within the ordinary skills of a trained physician or veterinary.

In the present context, treatment or treating mean the management and care of a patient or subject for the purpose of combating a condition, a disease or a disorder. The term is intended to include the full spectrum of treatments for a given condition from which the patient or subject is suffering, such as administration of the active compound to alleviate the symptoms or complications, to delay the progression of the disease, disorder or condition, to alleviate or relief the symptoms and complications, to improve patient's status or outcome, and/or to cure or eliminate the disease, disorder or condition as well as to prevent the condition, wherein prevention is to be understood as the management and care of a patient for the purpose of combating the disease, condition, or disorder and includes the administration of the active compounds to prevent or delay the onset of the symptoms or complications.

Within this invention it is to be understood that the combinations, compositions or combined uses according to this invention may envisage the simultaneous, sequential or separate administration of the active components or ingredients.

In this context, "combination" or "combined" within the meaning of this invention may include, without being limited, fixed and non-fixed (e.g. free) forms (including kits) and uses, such as e.g. the simultaneous, sequential or separate use of the components or ingredients.

The combined administration of this invention may take place by administering the active components or ingredients together, such as e.g. by administering them simultaneously in one single or in two separate formulations or dosage forms. Alternatively, the administration may take place by administering the active components or ingredients sequentially, such as e.g. successively in two separate formulations or dosage forms.

For the combination therapy of this invention the active components or ingredients may be administered separately (which implies that they are formulated separately) or formulated altogether (which implies that they are formulated in the same preparation or in the same dosage form). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

With respect to embodiment A, the methods of synthesis for the DPP-4 inhibitors according to embodiment A of this invention are known to the skilled person. Advantageously, the DPP-4 inhibitors according to embodiment A of this invention can be prepared using synthetic methods as described in the literature. Thus, for example, purine derivatives of formula (I) can be obtained as described in WO 2002/068420, WO 2004/018468, WO 2005/085246, WO 2006/029769 or WO 2006/048427, the disclosures of which are incorporated herein. Purine derivatives of formula (II) can be obtained as described, for example, in WO 2004/050658 or WO 2005/110999, the disclosures of which are incorporated herein. Purine derivatives of formula (III) and (IV) can be obtained as described, for example, in WO 2006/068163, WO 2007/071738 or WO 2008/017670, the disclosures of which are incorporated herein. The preparation of those DPP-4 inhibitors, which are specifically mentioned hereinabove, is disclosed in the publications mentioned in connection therewith. Polymorphous crystal modifications and formulations of particular DPP-4 inhibitors are disclosed in WO 2007/128721 and WO 2007/128724, respectively, the disclosures of which are incorporated herein in their entireties. Formulations of particular DPP-4 inhibitors with metformin or other combination partners are described in WO 2009/121945, the disclosure of which is incorporated herein in its entirety.

Typical dosage strengths of the dual fixed combination (tablet) of linagliptin/metformin IR (immediate release) are 2.5/500 mg, 2.5/850 mg and 2.5/1000 mg, which may be administered 1-3 times a day, particularly twice a day.

Typical dosage strengths of the dual fixed combination (tablet) of linagliptin/metformin XR (extended release) are 5/500 mg, 5/1000 mg and 5/1500 mg (each one tablet) or 2.5/500 mg, 2.5/750 mg and 2.5/1000 mg (each two tablets), which may be administered 1-2 times a day, particularly once a day, preferably to be taken in the evening with meal.

The present invention further provides a DPP-4 inhibitor as defined herein for use in (add-on or initial) combination therapy with metformin (e.g. in a total daily amount from 500 to 2000 mg metformin hydrochloride, such as e.g. 500 mg, 850 mg or 1000 mg once or twice daily).

With respect to embodiment B, the methods of synthesis for the DPP-4 inhibitors of embodiment B are described in the scientific literature and/or in published patent documents, particularly in those cited herein.

The elements of the combination of this invention may be administered by various ways, for example by oral, buccal, sublingual, enterical, parenteral (e.g., transdermal, intramuscular or subcutaneous), inhalative (e.g., liquid or powder inhalation, aerosol), pulmonary, intranasal (e.g. spray), intraperitoneal, vaginal, rectal, or topical routes of administration and may be formulated, alone or together, in suitable dosage unit formulations containing conventional non-toxic pharmaceutically acceptable carriers, adjuvants and vehicles appropriate for each route of administration.

In an embodiment, the DPP-4 inhibitor according to the invention is preferably administered orally.

Suitable doses and dosage forms of the DPP-4 inhibitors may be determined by a person skilled in the art and may include those described herein or in the relevant references.

For pharmaceutical application in warm-blooded vertebrates, particularly humans, the compounds of this invention are usually used in dosages from 0.001 to 100 mg/kg body weight, preferably at 0.01-15 mg/kg or 0.1-15 mg/kg, in each case 1 to 4 times a day. For this purpose, the compounds, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The pharmaceutical compositions according to this invention comprising the DPP-4 inhibitors as defined herein are thus prepared by the skilled person using pharmaceutically acceptable formulation excipients as described in the art and appropriate for the desired route of administration. Examples of such excipients include, without being restricted to diluents, binders, carriers, fillers, lubricants, flow promoters, crystallisation retardants, disintegrants, solubilizers, colorants, pH regulators, surfactants and emulsifiers.

Oral formulations or dosage forms of the DPP-4 inhibitor of this invention may be prepared according to known techniques.

A pharmaceutical composition or dosage form (e.g. oral tablet) of a DPP-4 inhibitor according to embodiment A of the invention may typically contain as excipients (in addition to an active ingredient), for example: one or more diluents, a binder, a disintegrant, and a lubricant, preferably each as disclosed herein-below. In an embodiment, the disintegrant may be optional.

Examples of suitable diluents for compounds according to embodiment A include cellulose powder, calcium hydrogen phosphate, erythritol, low substituted hydroxypropyl cellulose, mannitol, pregelatinized starch or xylitol.

Examples of suitable lubricants for compounds according to embodiment A include talc, polyethyleneglycol, calcium behenate, calcium stearate, hydrogenated castor oil or magnesium stearate.

Examples of suitable binders for compounds according to embodiment A include copovidone (copolymerisates of vinylpyrrolidon with other vinylderivates), hydroxypropyl methylcellulose (HPMC), hydroxypropylcellulose (HPC), polyvinylpyrrolidon (povidone), pregelatinized starch, or low-substituted hydroxypropylcellulose (L-HPC).

Examples of suitable disintegrants for compounds according to embodiment A include corn starch or crospovidone.

Suitable methods of preparing (oral) preparations or dosage forms of the DPP-4 inhibitors according to embodiment A of the invention are
  direct tabletting of the active substance in powder mixtures with suitable tabletting excipients;
  granulation with suitable excipients and subsequent mixing with suitable excipients and subsequent tabletting as well as film coating; or
  packing of powder mixtures or granules into capsules.
Suitable granulation methods are
  wet granulation in the intensive mixer followed by fluidised bed drying;
  one-pot granulation;
  fluidised bed granulation; or
  dry granulation (e.g. by roller compaction) with suitable excipients and subsequent tabletting or packing into capsules.

An exemplary composition (e.g. tablet core) of a DPP-4 inhibitor according to embodiment A of the invention comprises the first diluent mannitol, pregelatinized starch as a second diluent with additional binder properties, the binder copovidone, the disintegrant corn starch, and magnesium stearate as lubricant; wherein copovidone and/or corn starch may be optional.

A tablet of a DPP-4 inhibitor according to embodiment A of the invention may be film coated, preferably the film coat comprises hydroxypropylmethylcellulose (HPMC), polyethylene glycol (PEG), talc, titanium dioxide and iron oxide (e.g. red and/or yellow).

In a further embodiment, the DPP-4 inhibitor according to the invention may be administered by injection (preferably subcutaneously). In another embodiment, the GLP-1 receptor agonist is preferably administered by injection (preferably subcutaneously) as well.

Injectable formulations of the GLP-1 receptor agonist and/or the DPP-4 inhibitor of this invention (particularly for subcutaneous use) may be prepared according to known formulation techniques, e.g. using suitable liquid carriers, which usually comprise sterile water, and, optionally, further additives such as e.g. preservatives, pH adjusting agents, buffering agents, isotoning agents, solubility aids and/or tensides or the like, to obtain injectable solutions or suspensions. In addition, injectable formulations may comprise further additives, for example salts, solubility modifying agents or precipitating agents which retard release of the drug(s). In further addition, injectable GLP-1 formulations may comprise GLP-1 stabilizing agents (e.g. a surfactant).

For example, an injectable formulation (particularly for subcutaneous use) containing the GLP-1 receptor agonist (e.g. exenatide), optionally together with the DPP-4 inhibitor of this invention, may further comprise the following additives: a tonicity-adjusting agent (such as e.g. mannitol), an antimicrobial preservative (such as e.g. metacresol), a buffer or pH adjusting agent (such as e.g. glacial acetic acid and sodium acetate trihydrate in water for injection as a buffering solution at pH 4.5), and optionally a solubilizing and/or stabilizing agent (such as e.g. a surfactant or detergent).

In a further embodiment, the DPP-4 inhibitor according to the invention may be administered by a transdermal delivery system. In another embodiment, the GLP-1 receptor agonist is preferably administered by a transdermal delivery system as well.

Transdermal formulations (e.g. for transdermal patches or gels) of the GLP-1 receptor agonist and/or the DPP-4 inhibitor of this invention may be prepared according to known formulation techniques, e.g. using suitable carriers and, optionally, further additives. To facilitate transdermal passage, different methodologies and systems may be used, such as e.g. techniques involving formation of microchannels or micropores in the skin, such as e.g. iontophoresis (based on low-level electrical current), sonophoresis (based on low-frequency ultrasound) or microneedling, or the use of drug-carrier agents (e.g. elastic or lipid vesicles such as transfersomes) or permeation enhancers.

For further details on dosage forms, formulations and administration of DPP-4 inhibitors of this invention and/or GLP-1 receptor agonist of this invention, reference is made to scientific literature and/or published patent documents, particularly to those cited herein.

The pharmaceutical compositions (or formulations) may be packaged in a variety of ways. Generally, an article for distribution includes one or more containers that contain the one or more pharmaceutical compositions in an appropriate form. Tablets are typically packed in an appropriate primary package for easy handling, distribution and storage and for assurance of proper stability of the composition at prolonged contact with the environment during storage. Primary containers for tablets may be bottles or blister packs.

A suitable bottle, e.g. for a pharmaceutical composition or combination (tablet) comprising a DPP-4 inhibitor according to embodiment A of the invention, may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack, e.g. for a pharmaceutical composition or combination (tablet) comprising a DPP-4 inhibitor according to embodiment A of the invention, comprises or is formed of a top foil (which is breachable by the tablets) and a bottom part (which contains pockets for the tablets). The top foil may contain a metallic foil, particularly aluminium or aluminium alloy foil (e.g. having a thickness of 20 µm to 45 µm, preferably 20 µm to 25 µm) that is coated with a heat-sealing polymer layer on its inner side (sealing side). The bottom part may contain a multi-layer polymer foil (such as e.g. poly(vinyl chloride) (PVC) coated with poly (vinylidene choride) (PVDC); or a PVC foil laminated with poly(chlorotriflouroethylene) (PCTFE)) or a multi-layer polymer-metal-polymer foil (such as e.g. a cold-formable laminated PVC/aluminium/polyamide composition).

To ensure a long storage period especially under hot and wet climate conditions an additional overwrap or pouch made of a multi-layer polymer-metal-polymer foil (e.g. a laminated polyethylene/aluminium/polyester composition) may be used for the blister packs.

Supplementary desiccant (such as e.g. bentonite clay, molecular sieves, or, preferably, silica gel) in this pouch package may prolong the shelf life even more under such harsh conditions.

Solutions for injection may be available in typical suitable presentation forms such as vials, cartridges or prefilled (disposable) pens, which may be further packaged.

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

With respect to the first embodiment (embodiment A), the dosage typically required of the DPP-4 inhibitors mentioned herein in embodiment A when administered intravenously is 0.1 mg to 10 mg, preferably 0.25 mg to 5 mg, and when administered orally is 0.5 mg to 100 mg, preferably 2.5 mg to 50 mg or 0.5 mg to 10 mg, more preferably 2.5 mg to 10 mg or 1 mg to 5 mg, in each case 1 to 4 times a day. Thus, e.g. the dosage of 1-[(4-methyl-quinazolin-2-yl)methyl]-3-methyl-7-(2-butyn-1-yl)-8-(3-(R)-amino-piperidin-1-yl)-xanthine when administered orally is 0.5 mg to 10 mg per patient per day, preferably 2.5 mg to 10 mg or 1 mg to 5 mg per patient per day.

For example, doses of linagliptin when administered subcutaneously or i.v. for human patients are in the range of 0.3-10 mg, preferably from 1 to 5 mg, particularly 2.5 mg, per patient per day.

In a further embodiment, for example, doses of linagliptin when administered subcutaneously for human patients (such as e.g. in obese human patients or for treating obesity) are in the range of 0.1-30 mg, preferably from 1 to 10 mg, particularly 5 mg, per patient per day.

A dosage form prepared with a pharmaceutical composition comprising a DPP-4 inhibitor mentioned herein in embodiment A contain the active ingredient in a dosage range of 0.1-100 mg. Thus, e.g. particular oral dosage strengths of 1-[(4-methyl-quinazolin-2-yl)methyl]-3-methyl-7-(2-butyn-1-yl)-8-(3-(R)-amino-piperidin-1-yl)-xanthine are 0.5 mg, 1 mg, 2.5 mg, 5 mg and 10 mg.

With respect to the second embodiment (embodiment B), the doses of DPP-4 inhibitors mentioned herein in embodiment B to be administered to mammals, for example human beings, of, for example, approximately 70 kg body weight, may be generally from about 0.5 mg to about 350 mg, for example from about 10 mg to about 250 mg, preferably 20-200 mg, more preferably 20-100 mg, of the active moiety per person per day, or from about 0.5 mg to about 20 mg, preferably 2.5-10 mg, per person per day, divided preferably into 1 to 4 single doses which may, for example, be of the same size. Single oral dosage strengths comprise, for example, 10, 25, 40, 50, 75, 100, 150 and 200 mg of the DPP-4 inhibitor active moiety.

An oral dosage strength of the DPP-4 inhibitor sitagliptin is usually between 25 and 200 mg of the active moiety. A recommended dose of sitagliptin is 100 mg calculated for the active moiety (free base anhydrate) once daily. Unit dosage strengths of sitagliptin free base anhydrate (active moiety) are 25, 50, 75, 100, 150 and 200 mg. Particular unit dosage strengths of sitagliptin (e.g. per tablet) are 25, 50 and 100 mg. An equivalent amount of sitagliptin phosphate monohydrate to the sitagliptin free base anhydrate is used in the pharmaceutical compositions, namely, 32.13, 64.25, 96.38, 128.5, 192.75, and 257 mg, respectively. Adjusted dosages of 25 and 50 mg sitagliptin are used for patients with renal failure. Typical dosage strengths of the dual combination of sitagliptin/metformin are 50/500 mg and 50/1000 mg.

An oral dosage range of the DPP-4 inhibitor vildagliptin is usually between 10 and 150 mg daily, in particular between 25 and 150 mg, 25 and 100 mg or 25 and 50 mg or 50 and 100 mg daily. Particular examples of daily oral dosage are 25, 30, 35, 45, 50, 55, 60, 80, 100 or 150 mg. In a more particular aspect, the daily administration of vildagliptin may be between 25 and 150 mg or between 50 and 100 mg. In another more particular aspect, the daily administration of vildagliptin may be 50 or 100 mg. The application of the active ingredient may occur up to three times a day, preferably one or two times a day. Particular dosage strengths are 50 mg or 100 mg vildagliptin. Typical dosage strengths of the dual combination of vildagliptin/metformin are 50/850 mg and 50/1000 mg.

Alogliptin may be administered to a patient at an oral daily dose of between 5 mg/day and 250 mg/day, optionally between 10 mg and 200 mg, optionally between 10 mg and 150 mg, and optionally between 10 mg and 100 mg of alogliptin (in each instance based on the molecular weight of the free base form of alogliptin). Thus, specific oral dosage amounts that may be used include, but are not limited to 10 mg, 12.5 mg, 20 mg, 25 mg, 50 mg, 75 mg and 100 mg of alogliptin per day. Alogliptin may be administered in its free base form or as a pharmaceutically acceptable salt.

Saxagliptin may be administered to a patient at an oral daily dose of between 2.5 mg/day and 100 mg/day, optionally between 2.5 mg and 50 mg. Specific oral dosage amounts that may be used include, but are not limited to 2.5 mg, 5 mg, 10 mg, 15 mg, 20 mg, 30 mg, 40 mg, 50 mg and 100 mg of saxagliptin per day. Typical dosage strengths of the dual combination of saxagliptin/metformin are 2.5/500 mg and 2.5/1000 mg.

A special embodiment of the DPP-4 inhibitors of this invention refers to those orally administered DPP-4 inhibitors which are therapeutically efficacious at low dose levels, e.g. at oral dose levels <100 mg or <70 mg per patient per day, preferably <50 mg, more preferably <30 mg or <20 mg, even more preferably from 1 mg to 10 mg, particularly from 1 mg to 5 mg (more particularly 5 mg), per patient per day (if required, divided into 1 to 4 single doses, particularly 1 or 2 single doses, which may be of the same size, preferentially, administered orally once- or twice daily (more preferentially once-daily), advantageously, administered at any time of day, with or without food. Thus, for example, the daily oral amount 5 mg BI 1356 can be given in an once daily dosing regimen (i.e. 5 mg BI 1356 once daily) or in a twice daily dosing regimen (i.e. 2.5 mg BI 1356 twice daily), at any time of day, with or without food.

The dosage of the active ingredients in the combinations and compositions in accordance with the present invention may be varied, although the amount of the active ingredients shall be such that a suitable dosage form is obtained. Hence, the selected dosage and the selected dosage form shall depend on the desired therapeutic effect, the route of administration and the duration of the treatment. Dosage ranges for the combination may be from the maximal tolerated dose for the single agent to lower doses.

A particularly preferred DPP-4 inhibitor to be emphasized within the meaning of this invention is 1-[(4-methyl-quinazolin-2-yl)methyl]-3-methyl-7-(2-butyn-1-yl)-8-(3-(R)-amino-piperidin-1-yl)-xanthine (also known as BI1356 or linagliptin). BI1356 exhibits high potency, 24 h duration of action, and a wide therapeutic window. In patients with type 2 diabetes receiving multiple oral doses of 1, 2.5, 5 or 10 mg of BI 1356 once daily for 12 days, BI 1356 shows favourable pharmacodynamic and pharmacokinetic profile (see e.g. Table 3 below) with rapid attainment of steady state (e.g. reaching steady state plasma levels (>90% of the pre-dose plasma concentration on Day 13) between second and fifth day of treatment in all dose groups), little accumulation (e.g. with a mean accumulation ratio $R_{A,AUC} \leq 1.4$ with doses above 1 mg) and preserving a long-lasting effect on DPP-4 inhibition (e.g. with almost complete (>90%) DPP-4 inhibition at the 5 mg and 10 mg dose levels, i.e. 92.3 and 97.3% inhibition at steady state, respectively, and >80% inhibition over a 24 h interval after drug intake), as well as significant decrease in 2 h postprandial blood glucose excursions by ≥80% (already on Day 1) in doses≥2.5 mg, and with the cumulative amount of unchanged parent compound excreted in urine on Day 1 being below 1% of the administered dose and increasing to not more than about 3-6% on Day 12 (renal clearance $CL_{R,ss}$ is from about 14 to about 70 mL/min for the administered oral doses, e.g. for the 5 mg dose renal clearance is about 70 ml/min). In people with type 2 diabetes BI 1356 shows a placebo-like safety and tolerability. With low doses of about ≥5 mg, BI 1356 acts as a true once-daily oral drug with a full 24 h duration of DPP-4 inhibition. At therapeutic oral dose levels, BI 1356 is mainly excreted via the liver and only to a minor extent (about <7% of the administered oral dose) via the kidney. BI 1356 is primarily excreted unchanged via the bile. The fraction of BI 1356 eliminated via the kidneys increases only very slightly over time and with increasing dose, so that there will likely be no need to modify the dose of BI 1356 based on the patients' renal function. The non-renal elimination of BI 1356 in combination with its low accumulation potential and broad safety margin may be of significant benefit in a patient population that has a high prevalence of renal insufficiency and diabetic nephropathy.

TABLE 3

Geometric mean (gMean) and geometric coefficient of variation (gCV)
of pharmacokinetic parameters of BI 1356 at steady state (Day 12)

| Parameter | 1 mg gMean (gCV) | 2.5 mg gMean (gCV) | 5 mg gMean (gCV) | 10 mg gMean (gCV) |
|---|---|---|---|---|
| $AUC_{0-24}$ [nmol · h/L] | 40.2 (39.7) | 85.3 (22.7) | 118 (16.0) | 161 (15.7) |
| $AUC_{T,\,ss}$ [nmol · h/L] | 81.7 (28.3) | 117 (16.3) | 158 (10.1) | 190 (17.4) |
| $C_{max}$ [nmol/L] | 3.13 (43.2) | 5.25 (24.5) | 8.32 (42.4) | 9.69 (29.8) |
| $C_{max,\,ss}$ [nmol/L] | 4.53 (29.0) | 6.58 (23.0) | 11.1 (21.7) | 13.6 (29.6) |
| $t_{max}$* [h] | 1.50 [1.00-3.00] | 2.00 [1.00-3.00] | 1.75 [0.92-6.02] | 2.00 [1.50-6.00] |
| $t_{max,\,ss}$* [h] | 1.48 [1.00-3.00] | 1.42 [1.00-3.00] | 1.53 [1.00-3.00] | 1.34 [0.50-3.00] |
| $T_{1/2,\,ss}$ [h] | 121 (21.3) | 113 (10.2) | 131 (17.4) | 130 (11.7) |
| Accumulation $t_{1/2,}$ [h] | 23.9 (44.0) | 12.5 (18.2) | 11.4 (37.8) | 8.59 (81.2) |
| $R_{A,\,Cmax}$ | 1.44 (25.6) | 1.25 (10.6) | 1.33 (30.0) | 1.40 (47.7) |
| $R_{A,\,AUC}$ | 2.03 (30.7) | 1.37 (8.2) | 1.33 (15.0) | 1.18 (23.4) |
| $fe_{0-24}$ [%] | NC | 0.139 (51.2) | 0.453 (125) | 0.919 (115) |
| $fe_{T,\,SS}$ [%] | 3.34 (38.3) | 3.06 (45.1) | 6.27 (42.2) | 3.22 (34.2) |
| $CL_{R,\,ss}$ [mL/min] | 14.0 (24.2) | 23.1 (39.3) | 70 (35.0) | 59.5 (22.5) |

*median and range [min-max]
NC not calculated as most values below lower limit of quantification As different metabolic functional disorders often occur simultaneously, it is quite often indicated to combine a number of different active principles with one another. Thus, depending on the functional disorders diagnosed, improved treatment outcomes may be obtained if a DPP-4 inhibitor is combined with one or more active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors mentioned above—besides their use in mono-therapy—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners are metformin; sulphonylureas such as glibenclamide, tolbutamide, glimepiride, glipizide, gliquidon, glibornuride and gliclazide; nateglinide; repaglinide; mitiglinide; thiazolidinediones such as rosiglitazone and pioglitazone; PPAR gamma modulators such as metaglidases; PPAR-gamma agonists such as e.g. rivoglitazone, mitoglitazone, INT-131 and balaglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as GPR119 agonists (SMT3-receptor-agonists), such as the GPR119 agonists 5-ethyl-2-{4-[4-(4-tetrazol-1-yl-phenoxymethyl)-thiazol-2-yl]-piperidin-1-yl}-pyrimidine or 5-[1-(3-isopropyl-[1,2,4]oxadiazol-5-yl)-piperidin-4-ylmethoxy]-2-(4-methanesulfonyl-phenyl)-pyridine; 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757 (a PEGylated version of GLP-1), dulaglutide (LY-2189265), semaglutide or albiglutide; SGLT2-inhibitors such as e.g. dapagliflozin, sergliflozin (KGT-1251), atigliflozin, canagliflozin, ipragliflozin, luseogliflozin or tofogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as AS 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators such as e.g. [(3S)-6-({2',6'-dimethyl-4'-[3-(methylsulfonyl)propoxy]biphenyl-3-yl}methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

Metformin is usually given in doses varying from about 500 mg to 2000 mg up to 2500 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

For children 10 to 16 years of age, the recommended starting dose of metformin is 500 mg given once daily. If this dose fails to produce adequate results, the dose may be increased to 500 mg twice daily. Further increases may be made in increments of 500 mg weekly to a maximum daily dose of 2000 mg, given in divided doses (e.g. 2 or 3 divided doses). Metformin may be administered with food to decrease nausea.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (or up to 40 mg divided twice) a day (typical dosage strengths are 5 and 10 mg), or extended-release glibenclamide in doses from 5 to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily. (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals. Miglitol is usually given in doses from 25 to 100 mg with meals.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists such as e.g. {4-[(R)-2-ethoxy-3-(4-trifluoromethyl-phenoxy)-propylsulfanyl]-2-methyl-phenoxy}-acetic acid; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CBI antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

Further, the certain DPP-4 inhibitor of this invention may be used in combination with a substrate of DPP-4 (particularly with an anti-inflammatory substrate of DPP-4, such as a chemokine as mentioned below), which may be other than inkretins or GLP-1, for the purposes according to the present invention; such substrates of DPP-4 include, for example—without being limited to, one or more of the following:
Incretins:
    Glucagon-like peptide (GLP)-1
    Glucose-dependent insulinotropic peptide (GIP)

Neuroactive:
- Substance P
- Neuropeptide Y (NPY)
- Peptide YY

Energy homeostasis:
- GLP-2
- Prolactin
- Pituitary adenylate cyclase activating peptide (PACAP)

Other hormones:
- PACAP 27
- Human chorionic gonadotrophin alpha chain
- Growth hormone releasing factor (GHRF)
- Luteinizing hormone alpha chain
- Insulin-like growth factor (IGF-1)
- CCL8/eotaxin
- CCL22/macrophage-derived chemokine
- CXCL9/interferon-gamma-induced monokine Chemokines:
- CXCL10/interferon-gamma-induced protein-10
- CXCL11/interferon-inducible T cell a chemoattractant
- CCL3L1/macrophage inflammatory protein 1 alpha isoform
- LD78beta
- CXCL12/stromal-derived factor 1 alpha and beta Other:
- Enkephalins, gastrin-releasing peptide, vasostatin-1,
- peptide histidine methionine, thyrotropin alpha The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Survival of septic rats with and without linagliptin treatment:

Female Wistar rats are fed a diet containing 0.083 mg/kg linagliptin (corresponding to 50-150 nM mean plasma concentration) for 6 day or control diet. Animals are injected at day 2 with 10 mg/kg LPS (lipopolysaccharide) i.p. and observed for 4 additional days.

Three groups of female Wistar rats are compared with respect to proportion surviving 24 hours LPS (lipopolysaccharide, 10 mg/kg i.p.) treatment using Fisher's exact test for 2 by 3 tables (p=0.004), and additionally, group b and c are compared using Fisher's two-sided exact test for 2 by 2 tables (p=0.015, LPS vs. LPS+Linagliptin). It should be noted that the survival curve only represents preliminary data ("pseudo Kaplan-Meier-curve") since the exact time point of death of the rats is not assessed. The female Wistar rats are injected with LPS in the morning, monitored during the day and transferred back to the stable in the evening. Deaths are registered in the morning of the next day. Therefore, the septic rats in the LPS without linagliptin group die between 10 and 24 h (see black bar) upon injection of LPS. Rats on linagliptin receive a diet containing 0.083 mg/kg linagliptin (corresponding to 50-150 nM mean plasma concentration) 2 day before LPS injection.

No mortality is detected in linagliptin pretreated subjects but mortality in LPS treated subjects is about 28% (see FIG. 1).

Therefore, linagliptin is expected to reduce mortality and/or improve survival in subjects suffering from sepsis and/or SIRS.

FIG. 1 shows the survival of septic rats with and without linagliptin treatment.

In a similar experiment, on day 0 liraglutide (a stable GLP-1 analogue) in a dose of 200 µg/kg/d (s.c.), linagliptin (5 mg/kg/d, s.c., via osmotic Alzet pumps) and sitagliptin (50 mg/kg/d, s.c., via osmotic Alzet pumps) are each administered three days to male C57/BI6 mice to obtain steady state conditions. On day 4, lipopoly saccharide (LPS) from *Salmonella typhimurium* (*S. typh*, 17.5 mg/kg, i.p.) is injected and survivial is monitored over time (see FIG. 2). N=10 per group. The Gehan-Breslow-Wilcoxon-Test is used for statistical analysis of Kaplan-Meier curves, p values as indicated.

Figure 2:
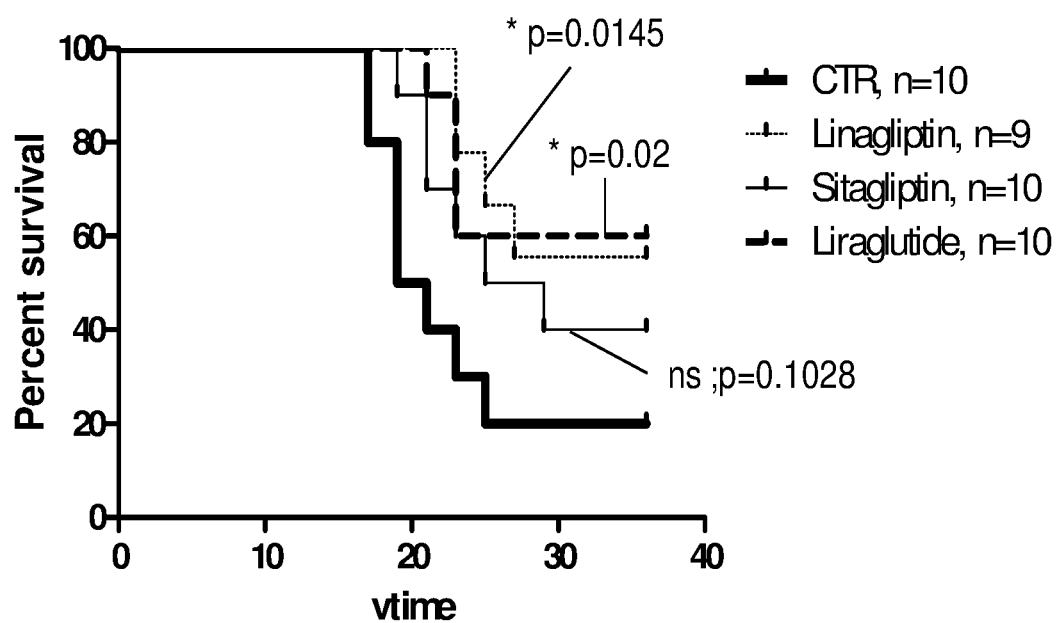
FIG. 2 shows the survival over time of septic mice under control, gliptin or GLP-1 treatment

FIG. 2 shows the survival over time of septic mice under control, gliptin or GLP-1 treatment.

Comparison of Linagliptin and Liraglutide on Survival in Experimental Sepsis

Background and aims: Gliptins (dipeptidyl peptidase [DPP]-4 inhibitors) are a newer class of drug for the treatment of hyperglycaemia. There is good evidence from studies in experimental atherosclerosis and septic animals that gliptins confer anti-inflammatory effects. Linagliptin therapy improves vascular dysfunction and vascular inflammation as well as aortic, cardiac, and blood oxidative stress in an experimental sepsis model. In addition, key findings from previous studies include the prevention of immune cell infiltration into the vascular tissue of septic animals by linagliptin therapy and the suppression of sepsis-induced increases in DPP-4 activity. The aim of this study is to determine the effect of linagliptin compared with the direct glucagon-like peptide (GLP)-1 analogue liraglutide on survival in different experimental models of septic shock.

Materials and methods: Mice (male C57BL/6, n=35-37 per group except n=10 for DPP-4-/-mice) are treated with linagliptin (5 mg/kg/d in the drinking water) or liraglutide (0.2 mg/kg/d by s.c. injection) for 7 days. On Day 6 of treatment, mice are injected with lipopoly saccharide (LPS, 20 mg/kg i.p.) to induce septic shock. In a second study, mice (n=9-10 per group) are infused for 3 days with the compounds by subcutaneously implanted osmotic minipumps (doses as described above). On Day 4 of treatment, the mice are injected with LPS 17.5 mg/kg i.p. DPP-4-/-mice serve as an additional control group. Survival is monitored over time. The Gehan-Breslow-Wilcoxon-Test is used for statistical analysis of Kaplan-Meier curves.

Results: In the placebo/LPS group, 100% of the mice die within the first 48 h following LPS injection. The survival of liraglutide treated mice is significantly improved (p=0.005) and linagliptin therapy shows a trend for a higher survival rate (p=0.067). As a proof of concept, the survival of DPP-4-deficient mice is significantly improved (p=0.002). To further explore these effects and the possibility of limited enteral drug absorption in sepsis, the subcutaneous infusion of all compounds is investigated. In the placebo/LPS group, 80% of the mice die within the first 36 h following LPS injection. The survival of linagliptin- and liraglutide treated mice is significantly improved (p=0.015 and p=0.02, respectively). Conclusion: The therapy of diabetic patients with linagliptin and liraglutide is well established. The results reported here on the improvement in the survival of septic animals could provide additional evidence for the potential use (preferably for parenteral drug application) of these drugs in patients with septic shock, who still have an overall mortality rate of 50%.

What is claimed is:

1. A method for treating systemic inflammatory response syndrome (SIRS) and/or sepsis (SIRS/sepsis) in a patient in need thereof, the method comprising administering to the patient a DPP-4 inhibitor which is of formula (I)

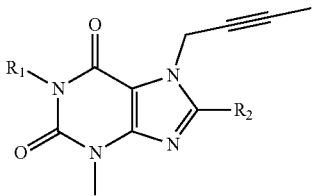

wherein R1 denotes (4-methyl-quinazolin-2-yl)methyl and R2 denotes 3-(R)-amino-piperidin-1-yl,
or a pharmaceutically acceptable salt thereof;
optionally in combination with one or more other active agents.

2. The method according to claim 1, wherein the method is for increasing survival rate and/or reducing mortality of a patient with SIRS and/or sepsis (SIRS/sepsis).

3. The method according to claim 1, wherein the patient has type 1, type 2 diabetes, or LADA.

4. The method according to claim 1, wherein the patient has type 2 diabetes mellitus.

5. The method according to claim 1, wherein the patient is non-diabetic.

6. The method according to claim 1, wherein the patient is impaired in renal function and/or has nephropathy and/or albuminuria.

7. The method according to claim 1, wherein SIRS/sepsis is one or more selected from septic or non-septic SIRS, severe SIRS/sepsis, SIRS/septic shock and multi-organ failure associated with SIRS/sepsis.

8. The method according to claim 1, wherein the method is characterized by increasing survival rate and/or reducing mortality of a patient with SIRS and/or sepsis (SIRS/sepsis).

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: C-terminal amidated cysteine

<400> SEQUENCE: 1

Val Glu Ile Cys
1